(12) United States Patent
Baker

(10) Patent No.: US 11,109,976 B2
(45) Date of Patent: Sep. 7, 2021

(54) MATERIAL COMPOSITIONS, APPARATUS AND METHOD OF MANUFACTURING COMPOSITES FOR MEDICAL IMPLANTS OR MANUFACTURING OF IMPLANT PRODUCT, AND PRODUCTS OF THE SAME

(71) Applicant: Dean Baker, Cypress, TX (US)

(72) Inventor: Dean Baker, Cypress, TX (US)

( * ) Notice: Subject to any disclaimer, the term of this patent is extended or adjusted under 35 U.S.C. 154(b) by 330 days.

(21) Appl. No.: 15/464,226

(22) Filed: Mar. 20, 2017

(65) Prior Publication Data

US 2017/0281827 A1 Oct. 5, 2017

Related U.S. Application Data

(60) Provisional application No. 62/310,483, filed on Mar. 18, 2016.

(51) Int. Cl.
| | |
|---|---|
| *A61F 2/30* | (2006.01) |
| *B33Y 80/00* | (2015.01) |
| *C08L 69/00* | (2006.01) |
| *B22F 1/02* | (2006.01) |

(52) U.S. Cl.
CPC .......... *A61F 2/30767* (2013.01); *B33Y 80/00* (2014.12); *A61F 2/30965* (2013.01); *B22F 1/02* (2013.01); *B22F 1/025* (2013.01); *C08L 69/00* (2013.01); *Y10T 428/12014* (2015.01); *Y10T 428/12181* (2015.01)

(58) Field of Classification Search
None
See application file for complete search history.

(56) References Cited

U.S. PATENT DOCUMENTS

| | | | |
|---|---|---|---|
| 4,536,158 A | * | 8/1985 | Bruins ............... A61K 6/08 260/998.11 |
| 6,207,218 B1 | | 3/2001 | Layrolle et al. |
| 6,733,503 B2 | | 5/2004 | Layrolle et al. |
| 6,854,172 B2 | | 2/2005 | Kaese et al. |
| 8,211,247 B2 | | 7/2012 | Marya et al. |
| 8,220,554 B2 | | 7/2012 | Jordan et al. |
| 8,342,094 B2 | | 1/2013 | Marya et al. |
| 8,409,289 B2 | | 4/2013 | Truckai et al. |
| 8,485,265 B2 | | 7/2013 | Marya et al. |
| 8,535,604 B1 | | 9/2013 | Baker et al. |
| 8,663,401 B2 | | 3/2014 | Marya et al. |
| 8,677,903 B2 | | 3/2014 | Marya et al. |
| 8,770,261 B2 | | 7/2014 | Marya |
| 8,986,369 B2 | | 3/2015 | Steckel et al. |
| 9,068,429 B2 | | 6/2015 | Mailand et al. |
| 9,079,246 B2 | | 7/2015 | Xu et al. |
| 9,090,956 B2 | | 7/2015 | Xu |

(Continued)

OTHER PUBLICATIONS

The Engineering ToolBox, "Electrode Potential and Galvanic Corrosion", <https://www.engineeringtoolbox.com/electrode-potential-d_482.html>, accessed Jul. 24, 2020.*

*Primary Examiner* — Xiaobei Wang

(74) *Attorney, Agent, or Firm* — Alberto Q. Amatong, Jr.; Amatong McCoy LLC

(57) ABSTRACT

A coated powder composite may include a core particle of Ca or an alloy thereof, or of Mg or an alloy thereof. One or more coating layers may be disposed about the core particle, cladding the core particle. The coated powder composite may be biodegradable.

22 Claims, 15 Drawing Sheets

(56) References Cited

U.S. PATENT DOCUMENTS

| | | |
|---|---|---|
| 9,109,429 B2 | 8/2015 | Xu et al. |
| 9,127,515 B2 | 9/2015 | Xu et al. |
| 9,333,099 B2 | 5/2016 | Pacetti et al. |
| 9,353,010 B2 | 5/2016 | McEntire et al. |
| 2004/0146543 A1* | 7/2004 | Shimp ................ A61L 27/3608 424/423 |
| 2006/0045787 A1* | 3/2006 | Jandeska, Jr. .......... B22F 1/025 419/47 |
| 2008/0249638 A1 | 10/2008 | Asgari |
| 2010/0294510 A1 | 11/2010 | Holmes |
| 2011/0135953 A1* | 6/2011 | Xu ............................ B22F 1/02 428/548 |
| 2012/0103135 A1 | 5/2012 | Xu et al. |
| 2012/0141775 A1* | 6/2012 | Ahmed ................... B22F 1/025 428/323 |
| 2013/0032357 A1* | 2/2013 | Mazyar ................... E21B 41/00 166/376 |
| 2014/0202708 A1 | 7/2014 | Jacob et al. |
| 2014/0228972 A1* | 8/2014 | Xu ........................... A61L 27/58 623/23.75 |
| 2014/0251641 A1 | 9/2014 | Marya et al. |
| 2014/0286810 A1 | 9/2014 | Marya |
| 2014/0363693 A1 | 12/2014 | Tamiya |
| 2017/0072465 A1 | 3/2017 | Welch et al. |
| 2017/0072471 A1 | 3/2017 | Welch et al. |

\* cited by examiner

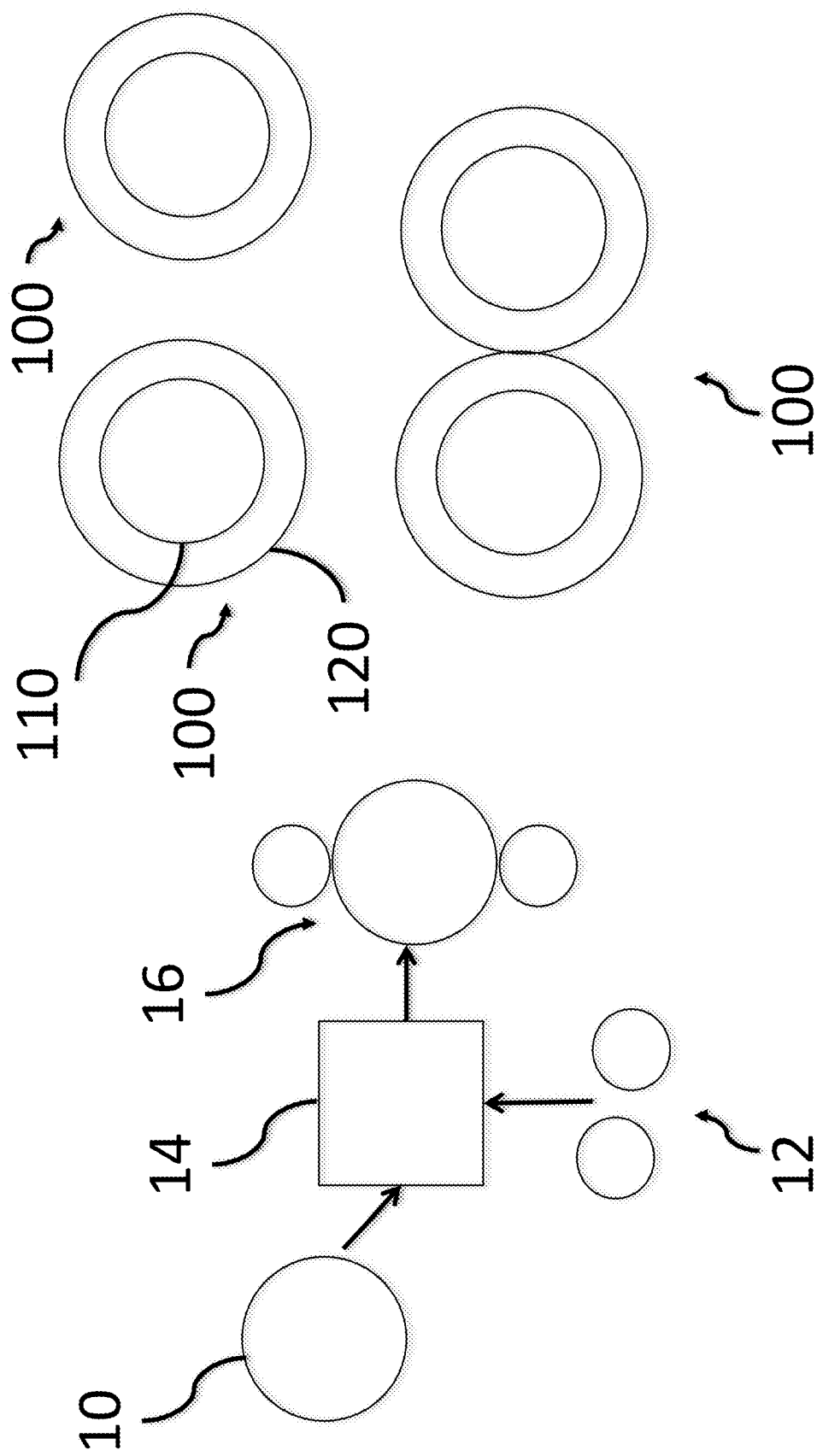

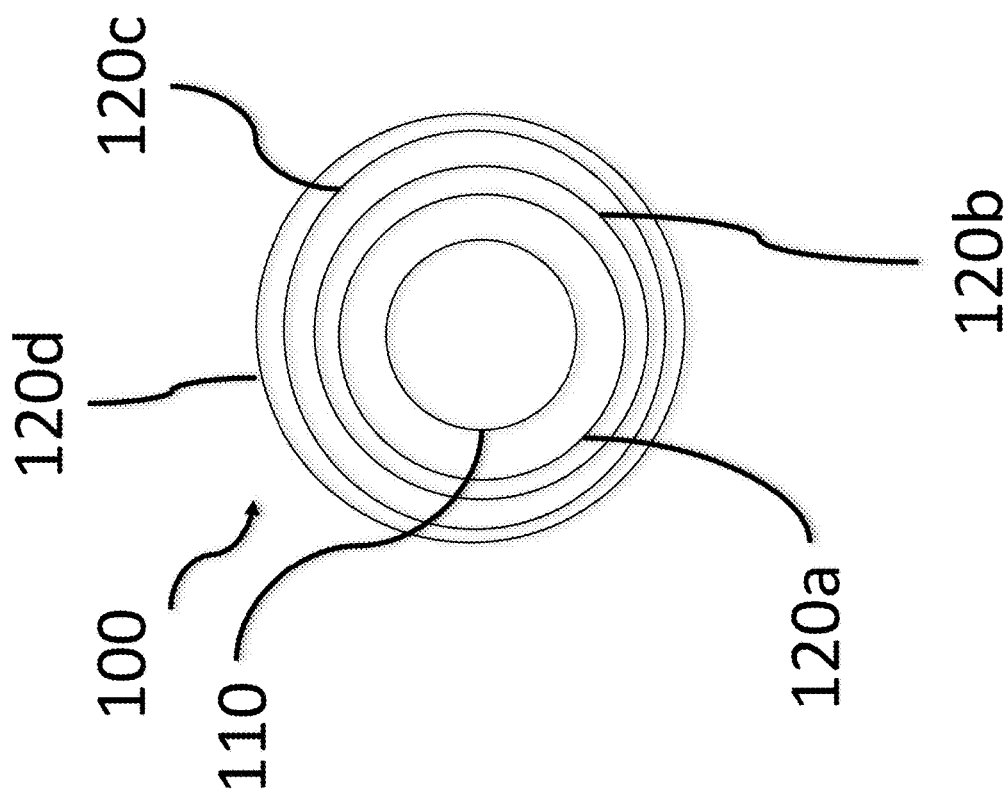

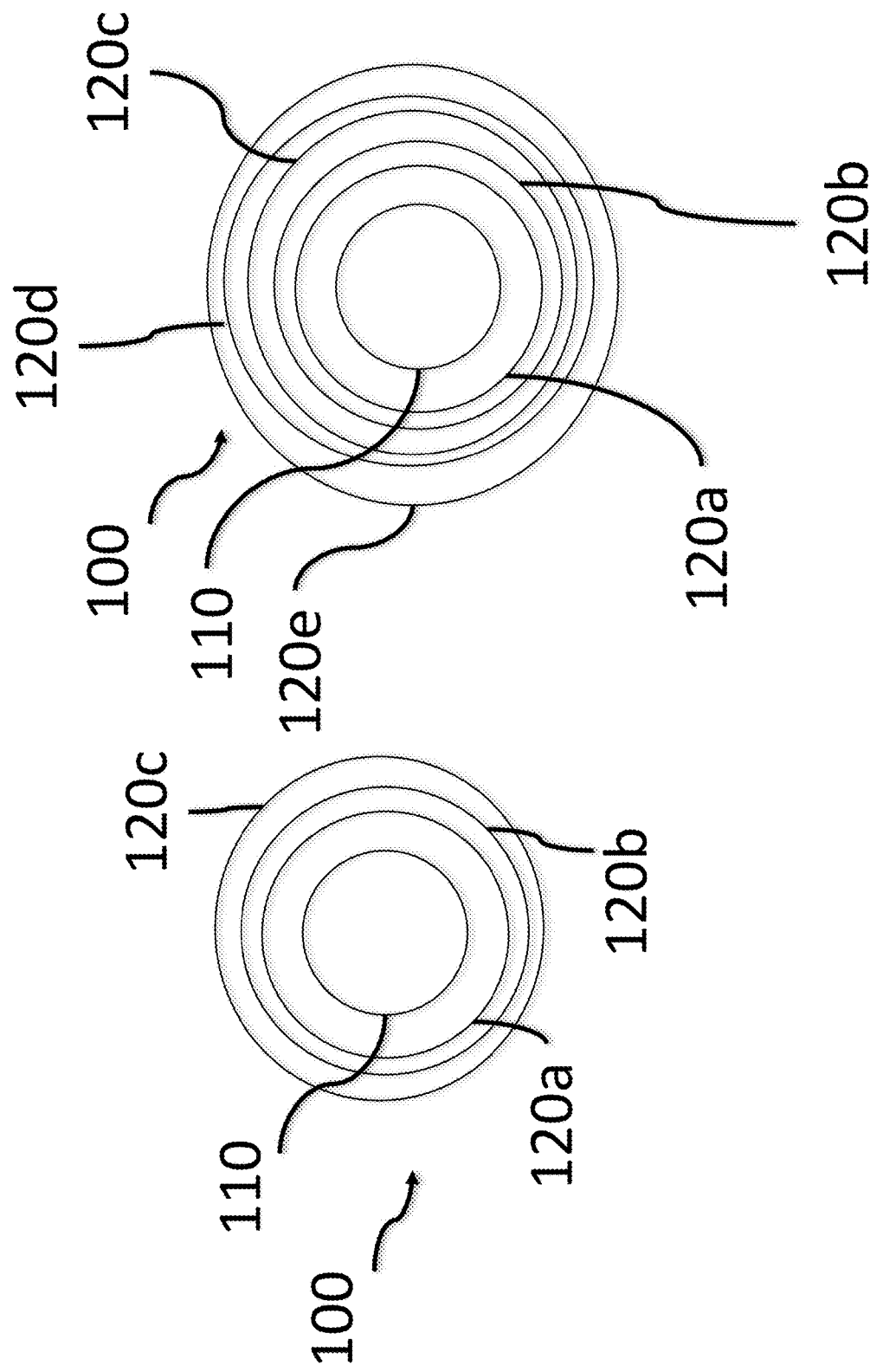

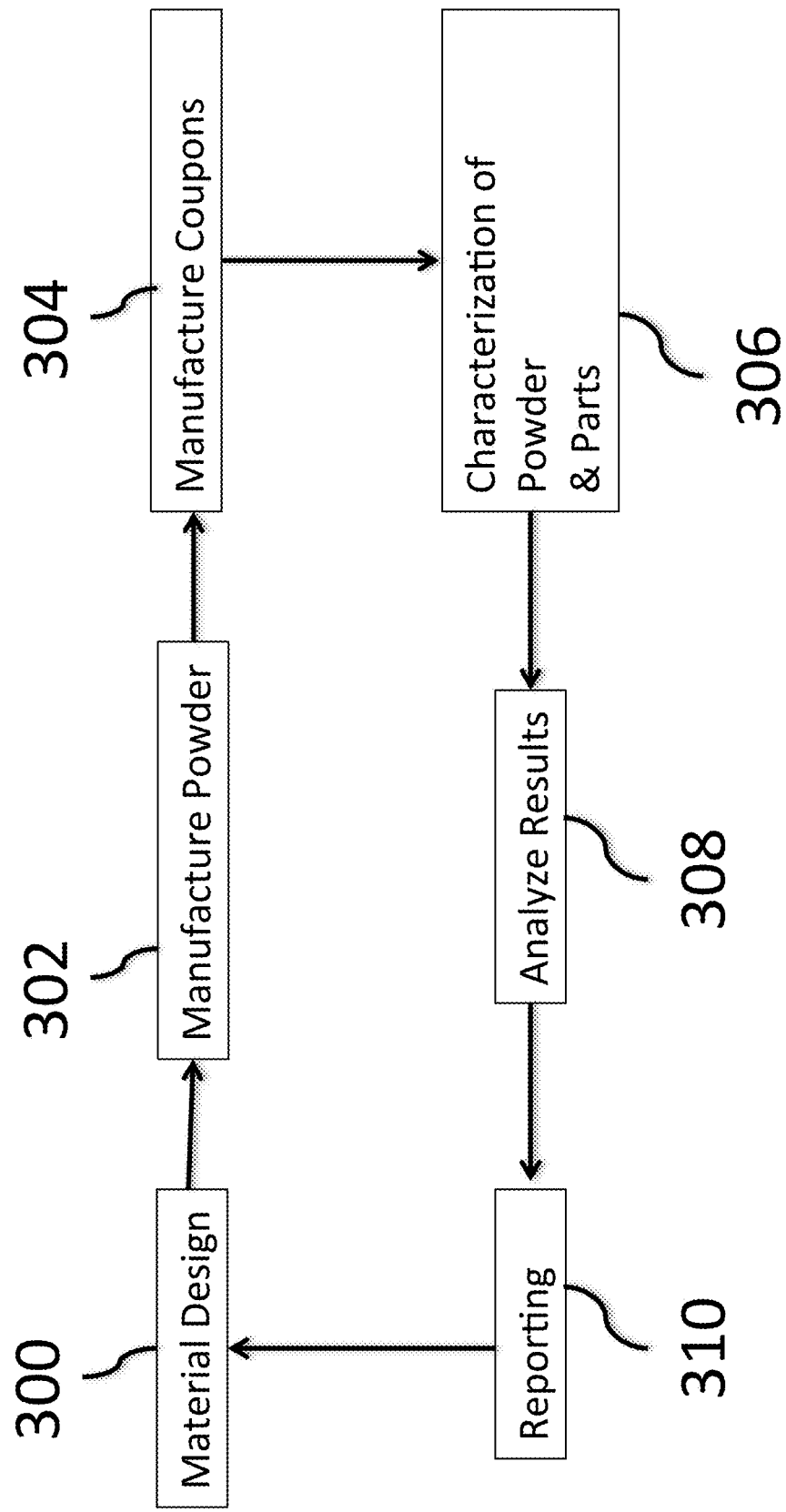

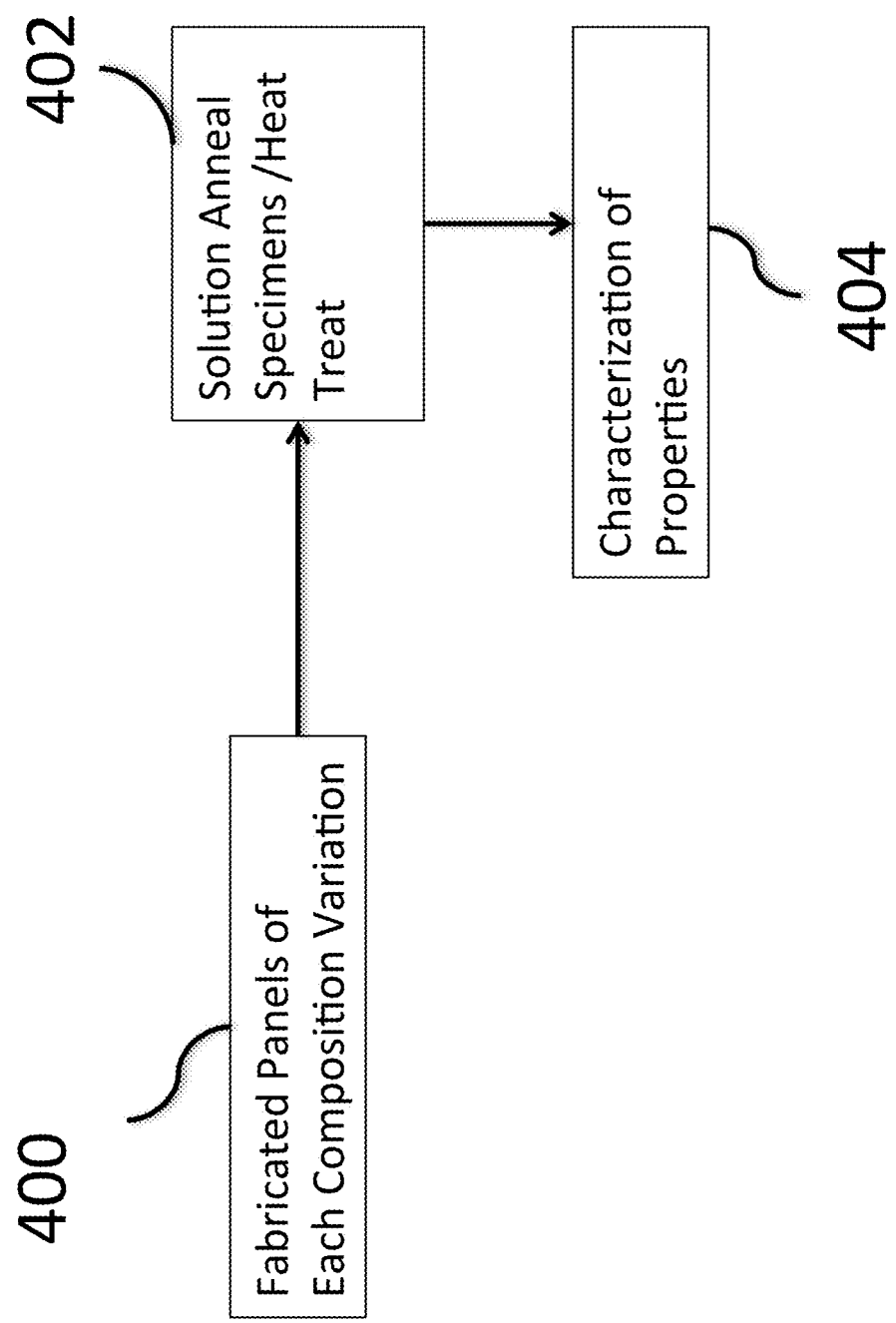

MATERIAL COMPOSITIONS, APPARATUS AND METHOD OF MANUFACTURING COMPOSITES FOR MEDICAL IMPLANTS OR MANUFACTURING OF IMPLANT PRODUCT, AND PRODUCTS OF THE SAME

CROSS-REFERENCE TO RELATED APPLICATIONS

The present application claims the benefit of U.S. Provisional Patent Application No. 62/310,483, filed on Mar. 18, 2016, the entirety of which is incorporated herein by reference for all purposes, and made a part of the present disclosure.

FIELD

The present disclosure relates generally to a material compositions, a high-strength composite, a product made of the composite or compositions, and methods of making the composite, compositions and\or the product, and apparatus for making same or employing the method. The present disclosure is particularly suited for\as medical or orthopedic implant products, and methods and apparatus of\for manufacturing the same. The apparatus, composite, products and methods are particularly adapted or applicable to orthopedic implants, e.g., a high medical implant product and method of making the same. The present disclosure also relates generally to a method of making such a product using coated powders and\or additive manufacturing techniques.

BACKGROUND

New and improved orthopedic implants are continually needed by the general population, particularly the elderly. Increased risks for osteoporosis, osteoarthritis and bone injuries, coupled with the desire to remain active later in life and the increase in obesity, will significantly increase the need for such implants. Although existing medical implants, and the materials from which these are made, are much improved from earlier designs, there is room for improvement. Weight bearing implants, from trauma fixation screws and alignment plates to hip and knee implants, are primarily made from metal, typically Titanium alloys (e.g., $Ti_6Al_4V$) or cobalt-chrome alloys. These designs often require revision and/or resurfacing surgery or removal surgery, resulting in higher medical costs and dramatically increasing patient discomfort and heal times.

Additive manufacturing is used to make a variety of implants, but is currently limited to use with Ti, Ni, or Co—Cr alloys, which can have compatibility issues.

BRIEF SUMMARY

In one aspect of the present disclosure, a method is provided for making a high-strength composite and\or a product made of the composite, and more particularly, a medical or orthopedic implant product. The method may include using or making a coated powder composite, and employing additive manufacturing techniques to form the product. In some embodiments, such a coated powder composite includes core particles that are coated and/or applied with one or more layers, each of which may be a property-specific layer. In certain embodiments, the coated powder composite may be magnesium (Mg) and/or aluminum (Al) based, e.g., the coated powder composite may include core particles that are Mg, Al, and\or alloys thereof. The coated powder composite, products, and methods disclosed herein may be adapted or applicable to orthopedic implants, e.g., a high medical implant product and a method of making same. The present disclosure also relates generally to a method of making such a product using coated powders and\or additive manufacturing techniques.

Certain embodiments relate to a coated powder composite. The coated powder composite may include a core particle of Ca or an alloy thereof, or of Mg or an alloy thereof. One or more coating layers may be disposed about the core particle, cladding the core particle. The coated powder composite may be biodegradable.

Each coating layer may include Mg, Sr, Ca, Zn, Si, Al, Fe, Ni, Ti, Cu, C, or combinations thereof.

In some embodiments, the coating layers may include an outermost layer. The outermost layer may be biocompatible, adapted for 3D printing, or combinations thereof. The outermost layer may include Ni, Fe, Ti, Cu, Si, Al, Co, C, Ca, Zn, or alloys thereof. The outermost layer may constitute from 0.5 to 10 weight percent of coated powder composite.

In some embodiments, the coating layers may include a dissolution activator layer. The dissolution activator may include Fe, Mg, C, Cu, or alloys thereof. The layer of dissolution activator may be from 0.001 to 8 weight percent of coated powder composite.

The coated powder composite may include one or more middle layers between the outermost layer and the innermost dissolution activator layer. The middle layers may include Al, Zn, $Al_2O_3$, Ca, Ti, C, Sr, or combinations thereof. The middle layer(s) may constitute from 0.1 to 10 weight percent of coated powder composite.

In some embodiments, each layer of the coatings exhibits electrical potential relative to adjacent layers of the coatings.

Certain embodiments relate to a method of making the composite and/or products therefrom. The method may include forming a coated powder composite by providing the core particle and depositing metal powders of the one or more coating layers onto the core particle. The depositing may include chemical vapor deposition. The method may include additive manufacturing a product from the coated powder composite. The product may be a medical implant.

Certain embodiments relate to a material composition for incorporation into a medical implant, including a matrix including a population of coated core particles, each core particle having one or more coating layers. The coating layers may include an external coating layer, a functional coating layer, and a dissolution activator coating layer adapted to induce galvanic corrosion. The functional coating layer may be an insulator layer.

The material composition may be characterized by a substantially uniform dissolution rate. As used herein, "substantially uniform dissolution rate" refers to a dissolution rate that has a substantially constant rate of change for at least a period of time. For example, with reference to FIG. 14, the derivative of the cure of the dissolution rate may be substantially constant. The functional coating layers may impart electrical insulation to the core particle from galvanic corrosion, mechanical strength to the coated core particle, or combinations thereof. In some embodiments, the core particle is made of bone material.

Certain embodiments relate to a medical implant made of the material composition. The medical implant may have a material composition comprising of matrix of coated core particles. The core particles may have an external coating layer (outermost layer), an activator coating layer (dissolution activator), and a functional coating layer (middle layers). The coating layers may be positioned such that said functional layer is disposed intermediate said external coating layer and said dissolution activator layer. The dissolution activator layer may be disposed adjacent said functional layer and said core particle.

BRIEF DESCRIPTION OF THE DRAWINGS

A more complete and thorough understanding of the present embodiments and advantages thereof may be acquired by referring to the following description taken in conjunction with the accompanying drawings.

FIG. 1A is a simplified illustration of a powder used in the prior art, and a method of making the same.

FIG. 1B is a simplified illustration of a powder in accordance with embodiments of the present disclosure, and a method of making the same.

FIGS. 2A-2C are simplified illustrations of a coated powder composite particle suitable for use in forming products, such as medical implants, in accordance with embodiments of the present disclosure.

FIG. 3 is a simplified flow chart of a process for developing coated powder composites and for achieving and/or controlling target properties in the coated powder composites in accordance with embodiments of the present disclosure.

FIG. 4 is a simplified flow chart of heat treatment and characterization for materials suitable for production of the coated powder composites in accordance with the present disclosure.

DETAILED DESCRIPTION

Figure 5B:
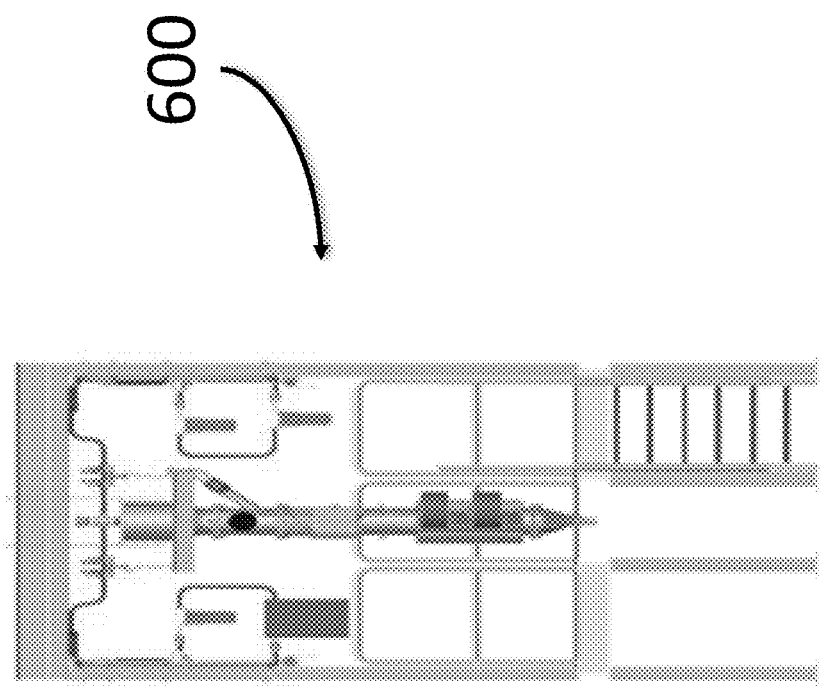
FIG. 5B is a simplified schematic a CVD fluid bed reactor suitable for use in applying coatings onto core particles of the coated powder composite in accordance with embodiment of the present disclosure.

Embodiments of the present disclosure will now be described more fully with reference to the accompanying drawings, which illustrate various exemplary embodiments. The disclosed concepts may, however, be embodied in many different forms and should not be construed as being limited by the illustrated embodiments set forth herein. Rather, these embodiments are provided so that this disclosure will be thorough as well as complete and will fully convey the scope to those skilled in the art and the best and preferred modes of practicing the embodiments. For example, many of the exemplary descriptions provided herein are concerned with coated powder composite particles for use in manufacturing into medical parts via additive manufacturing. Aspects of the disclosure described may, however, be equally applicable to designs for and the manufacture of other products. While products disclosed herein are described as medical implants, one skilled in the art would understand that the coated powder composite particles disclosed herein may be used to manufacture other articles, such as articles for use in downhole oil field applications. Further, while some embodiments of product are described as being manufactured via additive manufacturing techniques, one skilled in the art would understand that other manufacturing techniques may be employed when making products from coated powder composite particles disclosed herein. Additionally, the coated powder composite particles disclosed herein are not limited to the particular arrangements of layers provided herein, or the particular compositions of the layers described herein. Compositions described herein as forming the core particle and any of the coating layers may be replaced with other compositions that achieve the same and/or substantially similar results.

Embodiments of the present disclosure relate to coated powder composites suitable for use in product manufacturing via additive manufacturing techniques, to methods of making such coated powder composites, to methods of making products from such coated powder composites, and to products made from such coated powder composites.

Composite

FIG. 1A depicts a prior art method of making powder compositions. As shown in FIG. 1A, core particles 10 are be mixed/blended 14 with additive particles 12, forming mixture/blend 16. Core particles 10 and/or additive particles 12 may be solid powders, such as metal powders.

FIG. 1B depicts coated powder composites 100 in accordance with certain embodiments. Coated powder composites 100 include core particles 110 and one or more coatings 120 disposed about an outer surface of each core particle 110. Coatings 120 may be formed as layers, such as cladding, disposed about the outer surface of core particle 110.

In embodiments with multiple coatings 120, each coating 120 may be formed of the same composition as adjacent coatings 120 or of a different composition than adjacent coatings 120. Each coating 120 may be formed of the same composition as core particle 110 or of a different composition than core particle 110. Each coating 120 may be a metallic composition (e.g., single metal or alloy) or a ceramic (e.g., metal oxide) composition. In some embodiments, each coating 120 contains an alkaline earth metal, a transition metal, a post transition metal, or a metalloid. For example, each coating 120 may be formed of Mg or an alloy or oxide thereof, Sr or an alloy or oxide thereof, Ca or an alloy or oxide thereof, Zn or an alloy or oxide thereof, Si or an alloy or oxide thereof, Al or an alloy or oxide thereof, Fe or an alloy or oxide thereof, Ni or an alloy or oxide thereof, Ti or an alloy or oxide thereof, Cu or an alloy or oxide thereof, or Carbon (e.g., carbon coating). In some embodiments Ca used herein as a core particle 110 or layer of coating 120 may be sourced from crushed bone. In some embodiments the thickness of each layer of coatings 120 ranges from 5 nanometers to 1.5 microns, or from 10 nanometers to 1 micron, or from 100 nanometers to 900 nanometers, or from 200 nanometers to 800 nanometers, or from 300 nanometers to 700 nanometers, or from 400 nanometers to 600 nanometers. In some embodiments the thickness of all layers of coatings 120 combined ranges from 5 nanometers to 1.5 microns, or from 10 nanometers to 1 micron, or from 100 nanometers to 900 nanometers, or from 200 nanometers to 800 nanometers, or from 300 nanometers to 700 nanometers, or from 400 nanometers to 600 nanometers.

Core particle 110 may be a metallic composition (e.g., single metal or alloy) or a ceramic (e.g., metal oxide) composition. In some embodiments, core particle 110 contains an alkaline earth metal. For example, core particle 110 may be formed of magnesium or an alloy or oxide thereof, or calcium or an alloy or oxide thereof. In some embodiments, core particle 110 may be formed of an alloy containing magnesium and/or calcium. Core particle 110 may have a particle size ranging from about 5 microns to 200 microns, or from 8 microns to 150 microns, or form 10 microns to 135 microns, or from 25 microns to 100 microns, or from 50 microns to 75 microns.

Coated powder composites 100 may be engineered at the powder level by selectively varying which metal powders are used to form core particle 110 and which metal powders are used to form each coating 120. Altering the composition of the metal powders of core particle 110 and coatings 120 may alter the properties (e.g., mechanical, thermal, conductive, chemical prosperities) exhibited by coated powder composites 100 and products formed therefrom. In certain embodiments, core particle 110 is a ceramic core particle or metallic core particle. In embodiments in which core particle 110 is a ceramic core particle, coatings 120 (e.g., metal coatings) may impart metallic behavior to coated powder composites 100. For example, such embodiments may exhibit mechanical, thermal, conductive, and/or chemical prosperities of a metallic particle, while having a ceramic core. As such, coated powder composite 100 may include core particles 110 that are coated and/or applied with one or more property-specific layers, coatings 120. For example, coated powder composites 100 may be engineered at the powder level to be suitable for use in making certain products, such as medical implants, having high strength and degradable properties.

In some embodiments, coated powder composites 100 may be biodegradable and suitable for production of biodegradable, such as medical implants. Such products made from coated powder composites 100 may be adapted to biodegrade (e.g., dissolve and/or absorb) within the human body. In some embodiments, coatings 120 on core particles 110 may be adapted to degrade within the surrounding environment of the human body at a selected rate. For example, an outer layer of coatings 120 may be of a composition adapted to degrade at a first rate within the human body, one or more inner coatings 120 may be of a composition adapted to degrade at a second rate within the human body (faster than, equal to, or slower than the first rate), and core particle 110 may be of a composition adapted to degrade at a third rate within the human body (faster than, equal to, or slower than the first rate and/or the second rate). As such, the overall rate of degradation of coated powder composites 100 may be selectively controlled to have a desired residence time within the human body. In some embodiments, the residence time of coated powder composites 100 and/or products made therefrom within the human body ranges from 1 day to 12 months, or from 1 week to 11 months, or from 1 month to 10 months, or from 2 months to 9 months, or from 3 months to 8 months, or from 4 months to 7 months, or from 5 months to 6 months. Coated powder composites 100 may be biodegradable in accordance with standards established and/or set forth by the United States Food and Drug Administration (FDA), such that coated powder composites 100 degrade within the human body. Coated powder composites 100 may be biocompatible in accordance with standards established and/or set forth by the United States Food and Drug Administration (FDA), such that coated powder composites 100 are suitable for safe use within the human body (e.g., without causing allergic reaction and/or disease and/or other sickness).

Coated powder composites 100 may be a metal or ceramic microencapsulated powders. Core particles 110, in the form of ceramic or metal powder and/or particles, may be modified by applying one or more coatings 120 to achieve a target properties, e.g., in the form of a powder metal compact (PMC). The resultant properties of coated powder composites 100 may be at least partially defined by the properties of each coating 120, the interaction of the various coatings 120 (which may be applied in a series onto core particle 110), and the properties of core particle 110.

U.S. Pat. No. 8,535,604 provides background reference for exemplary suitable compositions and methods of production of the same that are suitable for use in certain embodiments of the present disclosure. As such, U.S. Pat. No. 8,535,604 (the '604 Patent) is hereby incorporated herein by reference, in its entirety and made a part of the present disclosure. In particular, FIGS. 1, 2, and 4 of the '604 Patent and the accompanying description thereof, show and describe compositions and methods of production thereof suitable for use in the present disclosure. In some embodiments, coated powder composite 100 and products made therefrom may exhibit corrosion resistance as described in the '604 Patent.

FIGS. 2A, 2B and 2C each depict coated powder composite 100 having multiple atomic layers (coatings 120), in accordance with different embodiments. Powder coated composite 100 may be achieved having controlled performance characteristics, such as strength, degradation rate, and other performance characteristics.

In the embodiment depicted in FIG. 2A, core particle 110 may be formed from a powder of or containing magnesium or an alloy or oxide thereof, or calcium or an alloy or oxide thereof. A first layer of coating 120a may be formed of or contain dissolution activator, which may be a compound or element capable of activating dissolution of coated powder composite 100 within the human body. One or more intermediate layers (intermediate of the layer containing the dissolution activator and the outermost, exterior layer of coated powder composite 100), such as second layer of coating 120b and third layer of coating 120c, may be formed of or contain a composition adapted to provide mechanical strength to coated powder composite 100 and/or a composition adapted to slow down the dissolution activator. A fourth layer of coating 120d may be formed of or contain a material adapted such that the coated powder composite 100 is suitable for use in additive manufacturing and/or is biocompatible for internal use within the human body. In some embodiments, the layers of coating 120 are selectively arranged to prove a controlled dissolution rate and conversion of, e.g., calcium, within the human body For example, in the embodiment depicted in FIG. 2B, core particle 110 may be formed from a powder of or containing magnesium or an alloy thereof. A first layer of coating 120a may be formed of or contain strontium. A second layer of coating 120*b* may be formed of or contain calcium. A third layer of coating 120*c* may be formed of or contain silicon.

In the embodiment depicted in FIG. 2C, core particle 110 may be formed from a powder of or containing magnesium or an alloy thereof. A first layer of coating 120*a* may be formed of or contain strontium. A second layer of coating 120*b* may be formed of or contain calcium. A third layer of coating 120*c* may be formed of or contain magnesium or an alloy thereof. A fourth layer of coating 120*d* may be formed of or contain zinc or an alloy thereof. A fifth layer of coating 120*e* may be formed of or contain silicon.

In some embodiments, core particle 110 may contain Ca or an alloy or oxide thereof or Mg or an oxide or alloy thereof. In some embodiments, core particle 110 may contain from 80 to 97 weight percent of Ca or an alloy thereof, or from 85 to 95 weight percent of Ca or an alloy thereof. In some embodiments, core particle 110 may contain from 90 to 99 weight percent of Mg or an alloy thereof, or from 92 to 97 weight percent of Mg or an alloy thereof.

Some examples of outermost layer may be adapted for AM processing, such as Ni, Fe, Ti, Cu, Si, Al, Co, C, Ca, Zn, or alloys thereof. The outermost layer of coated powder composite 100 may constitute from 0.5 to 10 weight percent of coated powder composite 100, or from 1 to 7 weight percent of coated powder composite 100, or from 2 to 5 weight percent of coated powder composite 100.

The middle layers of coated powder composite 100 may contain Al, Zn, Al2O3, Ca, Ti, C, Sr, or combinations thereof. The middle layer(s) of coated powder composite 100 may constitute from 0.1 to 10 weight percent of coated powder composite 100, or from 0.3 to 7 weight percent of coated powder composite 100, or from 2 to 5 weight percent of coated powder composite 100.

Coated powder composite 100 may include one or more middle layers of dissolution activator. Dissolution activators suitable for use herein may include Fe, Mg, C, Cu, or alloys thereof. The layer of dissolution activator may form from 0.001 to 8 weight percent of coated powder composite 100, or from 0.01 to 7 weight percent of coated powder particle 100, or from 0.1 to 6 weight percent of coated powder composite 100, or from 1 to 5 weight percent of coated powder composite 100. The layer of dissolution activator may function to control the rate of dissolution of coated powder particle 100.

One example of a middle layer suitable for use herein is aluminum or an Al—Zn alloy. For example, an alloy of Al and Zn at a weight ratio of Al to Zn of 3:1 may be suitable for providing mechanical strength to coated powder particle 100.

The magnesium powder suitable for use in coated powder composites 100 may have a melting point of 650° C. and a boiling point of 1120° C. The magnesium powder may be a raw powder of magnesium having a particle size ranging from about 5 to 100 microns, for example. The silicon suitable for use in coated powder composites 100 may have a melting point of 1423° C. and a boiling point of 2355° C. The calcium suitable for use in coated powder composites 100 may have a melting point of 850° C. and a boiling point of 1487° C. The strontium suitable for use in coated powder composites 100 may have a melting point of 770° C. and a boiling point of 1367° C. The zinc suitable for use in coated powder composites 100 may have a melting point of 416° C. and a boiling point of 907° C.

In some embodiments, the outermost layer of powder coated composite 100 may be designed to have a surface chemistry that allows for additive manufacturing devices to be used in manufacturing with powder coated composite 100, enabling, e.g. Mg, to be consolidated.

In some embodiments, powder coated composite 100 is porous. In other embodiments, powder coated composite 100 is not porous, i.e., is non-porous.

In some embodiments, core particle 110 is 80 to 99.9 weight percent of coated powder composite 100 based on a total weight of coated powder particle, or from 85 to 99 weight percent, or from 90 to 98 weight percent, or from 95 to 97 weight percent. Coatings 120 may be from 0.1 to 20 weight percent of coated powder composite 100 based on the total weight of coated powder particle, or from 1 to 15 weight percent, or from 2 to 10 weight percent, or from 3 to 5 weight percent.

Method of Making the Composite

Certain embodiments of the present disclosure relate to a method of making composites. Such embodiments may be used to make coated powder composite 100. In certain embodiments, the method of making composites enables the economical, large-scale, nano-engineering of coated powdered composite 100, such as through the use of specialty powders (i.e., metal powders).

In some embodiments, the method includes designing, developing, manufacturing and/or testing one or more powder combinations to make different embodiments of coated powder composite 100, such as for use in additive manufacturing of bio-degradable medical implants. Coated powder composite 100 (e.g., Mg encapsulated powders) may be designed at the powder level to allow for controlled manufacturing via AM and tailorable properties and/or performance characteristics of coated powder composite 100 or products made therefrom (e.g., tailorable degradation rates for improved patient specific therapies). In some embodiments, coated powder composite 100 (e.g., Mg encapsulated powders) may be designed to have a high strength and/or controllable porosity.

With reference to FIG. 3, in some embodiments the method of making the composite includes material design step, 300. For example, one or more specific powders may be selected to form core particle 110 with a specific arrangement of layers of coating 120, to provide coated powder composite 100 with properties suitable for additive manufacturing. For example, metals or ceramics thereof or alloys thereof may be selected and/or designed based, at least in part, upon thermodynamic and kinetic modeling thereof of potential to yield the suitable properties for use in additive manufacturing. Certain materials design parameters that may be considered in material design step 300 include, but are not limited to: phase stability, oxide stability, precipitate and microstructural evolution as a function of heat treatment, and reactivity. Other parameters that may be considered in material design step 300 include, but are not limited to, elemental toxicity, which may be taken into account during the metal and/or ceramic and/or alloy selection process. Properties of selected materials for use in forming coated powder composite 100, as well as processing treatments thereof, may be simulated using tools such as the ThermoCalc Prisma (TC-PRISMA) software program, which may be used to predict precipitate density and size as a function of heat treatment, for example. The ThermoCalc DICTRA program may be used to simulate solute diffusion in order to determine oxides on the surface of the powder metal composites.

After material design step 300, the method includes a manufacture powder step, 302, in which the selected powder metals are used to form coated powder composite 100. The powder metals may be formed into coated powder composite 100 using chemical vapor deposition, as is described in more detail below. After, manufacture powder step 302, the method includes a manufacture coupons via additive manufacturing step, 304, in which coated powder composite 100 is formed, via additive manufacturing, into test coupons, as described in more detail below. In some embodiments, after AM fabrication of test coupons in step 304, the method includes heat-treating the test coupons. A standard development cycle for materials is shown in FIG. 4. In step 400 of FIG. 4, fabricated panels of each composition variation for use in coated powder composite 100 may be produced, which may then be heat treated via solution annealing in step 402. Solution annealing may include placing the samples (e.g., fabricated panels) into a solution at a temperature, such as 200° C., for a residence time, such as 2 hours. In some embodiments, three samples of each composition may be formed and characterized. At each stage in the standard development cycle for materials, the method may include characterization of one or more properties of the samples, including but to limited to mechanical properties, such as tensile properties, compressive prosperities, fatigue properties; thermal properties (e.g., coefficient of thermal expansion, CTE); conductivity properties; environmental exposure properties; and chemical properties (e.g., chemical analysis). As such, the method may provide the ability to create materials that meet or exceed the desired properties for a specific application. General property requirements and performance for certain common medical materials are shown in Table 1, below, and compared with property data for an AM processed APS Mg composites, formed using a modified direct energy system.

different metal interlayers (layers of coating 120) are applied between two different powders (e.g., two different Mg based powders) that form core particle 110 and outermost layer of coating 120 respectively, and are optimized for the AM processing.

In some embodiments, one or more interfacial layers (layers of coating 120) are applied that increase ductility of coated powder composite 100, aid in consolidation of coated powder composite 100, control surface reactions and melting of coated powder composite 100, or combinations thereof. In certain embodiments, coating 120 enhances coated powder composite 100 flow and wetting characteristics. In some embodiments of manufacture powder step 302, the interlayers of coating 120 are allowed to react or be separated to determine the consolidation characteristics and microstructure of the interlayers. In certain embodiments, the amount of and or thickness of material (metal) for core particle 110 and each layer of coating 120 are selected to provide desired strength and internal stress characteristics in coated powder composite 100.

The selection of materials (e.g., metal powders) for use in coated powder composite 100 may be based on many factors. For example and without limitation, calcium in coated powder composite 100 may promote bone formation, diminish bone resorption, and increase bone trabecular volume. Strontium in coated powder composite 100 may increase bone formation and diminish bone resorption. Silicon in coated powder composite 100 may enhance and/or promote calcination, enhance and/or promote healing, provide grain refinement, and/or increase strength and ductility of alloys in which it is contained. Silicon may also provide

TABLE 1

Comparison of Various Implant Materials to Natural Bone and AM

| Property | Natural Bone | APS AM Mg | Mg (wrought) | Ti Alloy | Co—Cr alloy | Stainless Steel | Synthetic Hydroxyapatite |
|---|---|---|---|---|---|---|---|
| Density (g/cm³) | 1.8-2.1 | 1.6-1.78 | 1.74-2.0 | 4.4-4.5 | 8.3-9.2 | 7.9-8.1 | 3.1 |
| Tensile Modulus (GPa) | 3-20 | 40-55 | 41-45 | 110-117 | 230 | 189-205 | 73-117 |
| Fracture Toughness (MPam$^{1/2}$) | 3-6 | 30-45 | 15-40 | 55-115 | Not Applicable | 50-200 | 0.7 |
| Compression Yield Strength (MPa) | 130-180 | 132-148 | 65-100 | 758-1117 | 450-1000 | 170-310 | 600 |

The powder used for the AM processed APS Mg composite, processed using a direct energy system as shown in Table 1, was a powder of: Mg, Zn, Al, and % Si. While the example powder (AM processed APS Mg composite) in Table 1 in accordance with embodiments of the present disclosure are processed using a direct energy system, powders in accordance with the present disclosure may also be AM processed using, for example, a Concept Laser available from GmbH or a robotic laser machine, such as the one at Wayne State University, or other AM systems. The method may be used to form specific powder designs by varying the core particle 110 compositions, powder layering sequence of coating 120, and final porosity levels, for example. With further reference to FIG. 3, in material design step 300, detailed material requirements may be determined, including testing required and potential heat treat cycles.

In manufacture powder step 302, nano-coated, engineered powders may be formed. In some embodiments, one or more suitable characteristics to coated powder composite 100 for processing via additive manufacturing.

Due, at least one part, to the hexagonal close packed (HCP) crystal structure, it may be difficult to make magnesium components using conventional processes. External layers of magnesium may have a low melting point of 650° C., a boiling point of 1120° C., and a high vapor pressure. Such properties may make it difficult to make Mg compositions/alloys via additive manufacturing techniques (e.g., DMLS or EBM). However, using Si in coated powder composite 100, such as in the outermost layer thereof, may overcome such difficulties of additive manufacturing of magnesium. In operation, a laser or electron beam may partially melt the surface silicon of embodiments of coated powder composite 100 and subsequent conduction and radiation heat may melt the Mg—Ca—Sr alloy for fabrication of coupons or products on a layer-by-layer basis (e.g., as per a CAD/STL file).

Figure 5A:
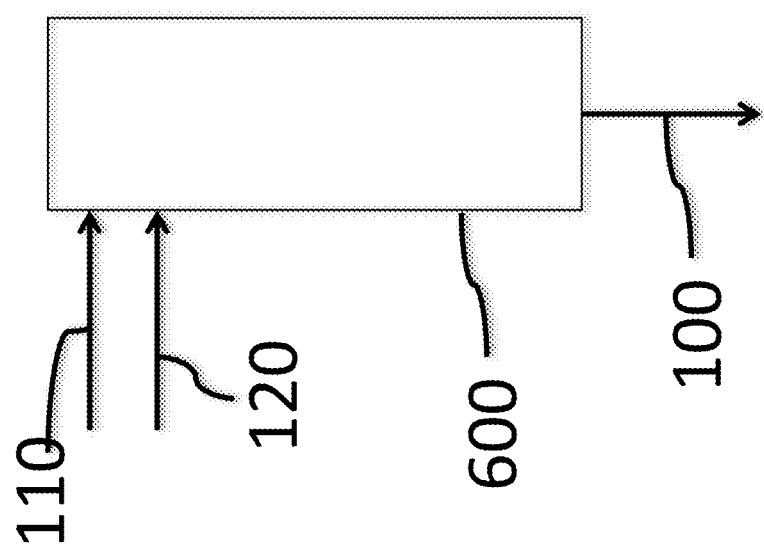
FIG. 5A is a simplified illustration a chemical vapor deposition (CVD) fluid bed reactor suitable for use in applying coatings onto core particles of the coated powder composite in accordance with embodiment of the present disclosure.

In some embodiments, powder layering of coated powder composite 100 may be achieved using a Chemical Vapor Deposition (CVD) Fluidized Bed unit 600, such as is shown in FIGS. 5A and 5B. Use of the CVD process enables formation of powder layering from core particle 110 and powders used to form coatings 120, while the fluid bed system allows each core particle 110 to be coated efficiently and uniformly without agglomeration. In some embodiments, silane may be used as a precursor for Si, diethyl zinc may be used as a precursor to Zn, calcium bis(2,2,6,6-tetramethyl-3,5-heptanedionate as a precursor for Ca, BEM may be used as a precursor to Mg, and strontium tetramethylheptanedionate may be used as a precursor to Sr, each for use in CVD processing.

In the manufacture powder step 302, several different encapsulated powders may be produced in amounts suitable for evaluation (e.g., 15 pounds).

Figure 6:
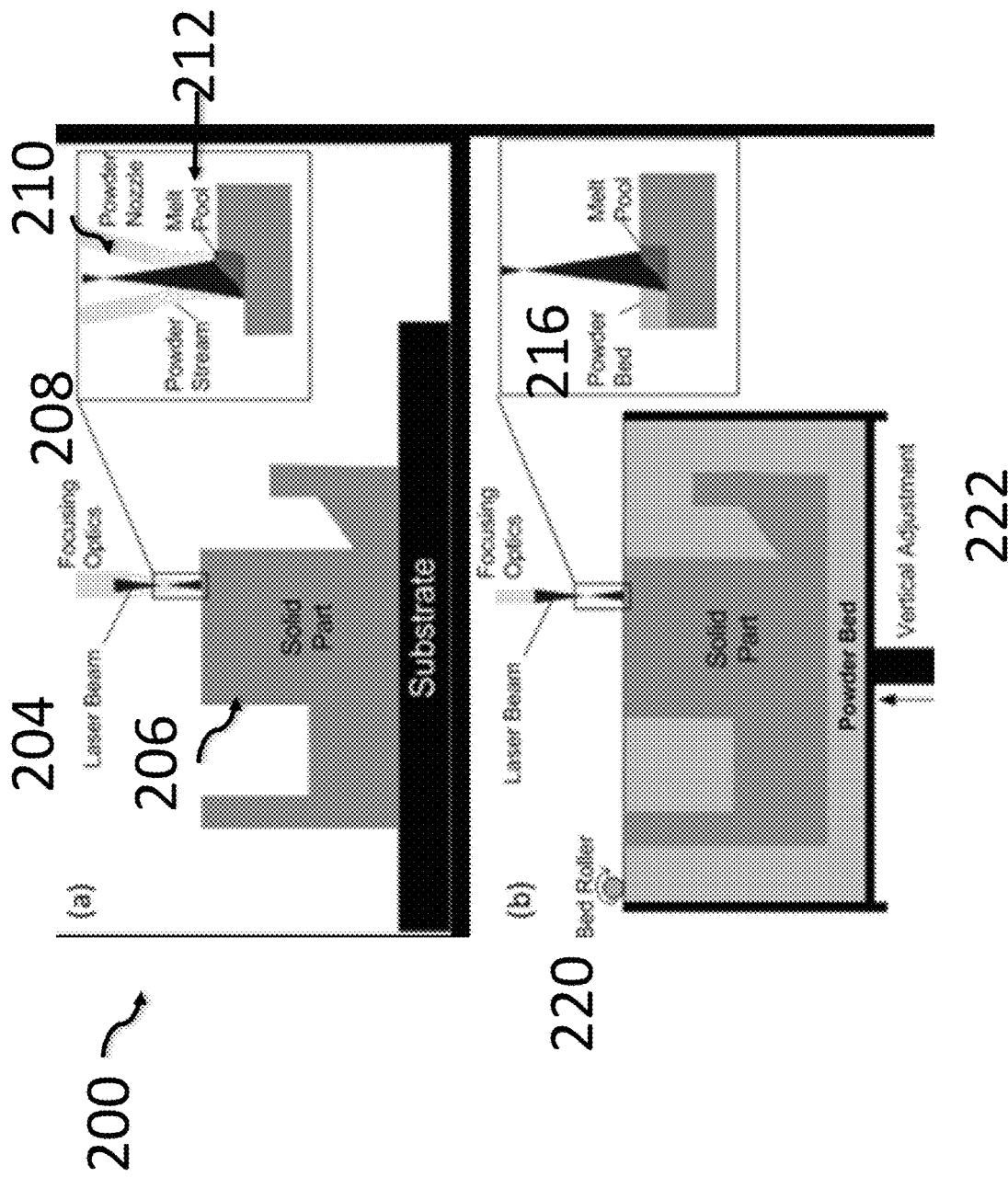
FIG. 6 is a simplified illustration of an additive manufacturing (AM) process and system, such as a Direct Laser Metal Laser Melting (DLM or DLML), suitable for use in manufacturing products from coated powder composites in accordance with embodiments of the present disclosure.
Figure 7:
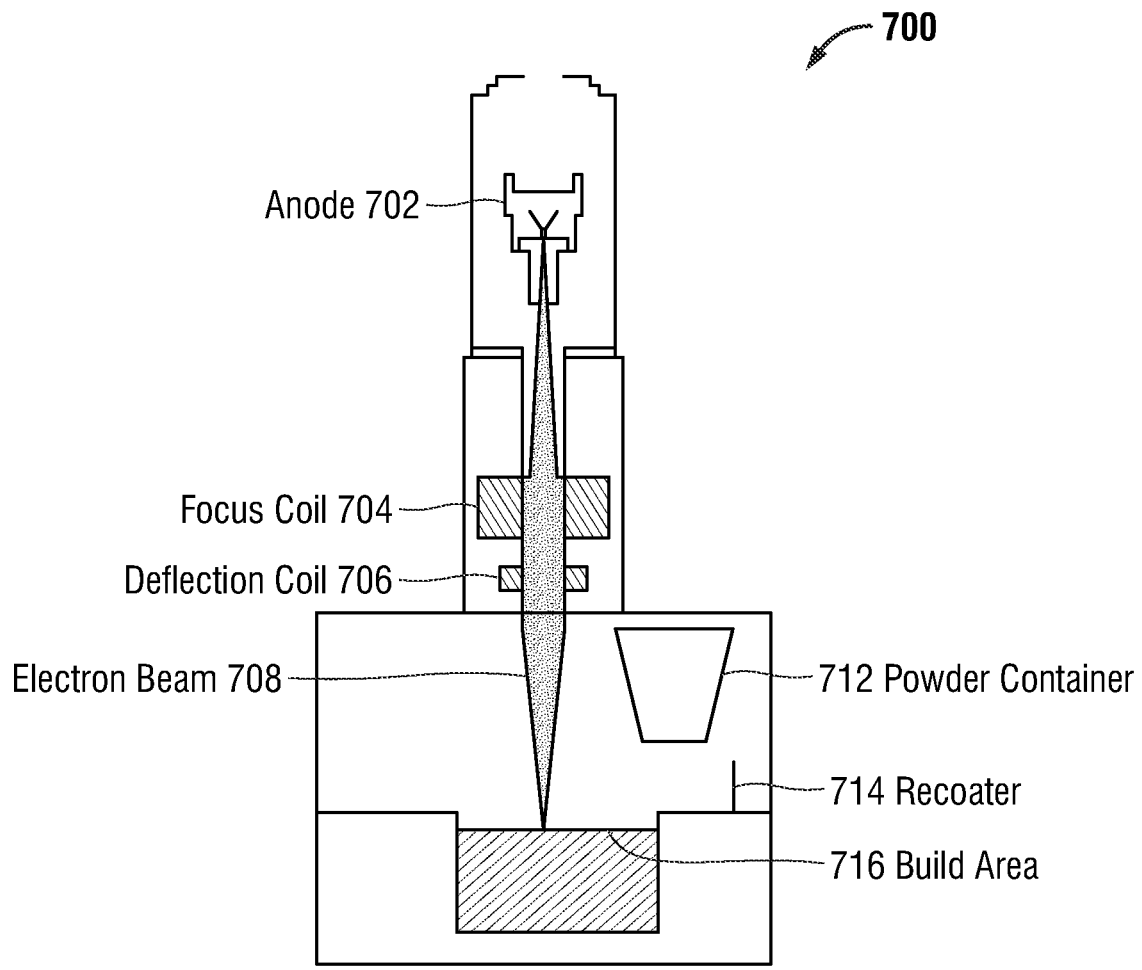
FIG. 7 is a simplified schematic an electron beam melting (EBM) system and process suitable for use in additive manufacturing of products from the coated powder composite in accordance with embodiment of the present disclosure.

In step 306, two AM systems were used for fabrication, including a Direct Metal Laser (DML) system 200, as shown in FIG. 6, and an electron beam melting (EBM) system 700, as shown in FIG. 7.

DML system 200 may be capable of producing near net shape components with complex shapes and thin structural walls. In DML processing, also referred to as selective laser melting (SLM), metallic powders 202 are melted by a laser 204 and "build" up occurs on a layer-by-layer basis to produce dense, solid parts 206 (e.g., metal parts) on a substrate 218. Each layer may be melted to the exact geometry defined by, e.g., a 3D CAD model. The laser beam 204 traces the pattern of the first layer, then the second layer, and the melted areas of the two layers are joined after re-solidification. The DML processing continues until the part is finished. Laser beam 204 may be focused via focusing optics 208. Metallic powders 202 may be provided from a powder nozzle 210. Laser beam 204 contacts metallic powders 202 in powder bed 216, forming melt pool 212. Metallic powders 202 may be spread to form powder bed 216, such as by using bed roller 220. Vertical adjustment 222 may allow for vertical positioning during formation of solid part 206.

In EBM system 700 may include anode 702, focus coil 704 and deflection coil 706, and may produce electron beam 708. Metallic powder may be provided from powder container 712. In the EBM process, components may be fabricated in a vacuum at elevated temperatures. As a result, stress-relieved parts may be produced with better material properties than cast parts, and may have material properties comparable to or equal to wrought materials. Electron beam 708 may be controlled by coils 704 and 706, without use of optics and/or moving mechanical parts, resulting in very good electron beam 78 control and extremely fast electron beam 708 translation. EBM system 700 may provide a high-energy electron beam 708, which allows for high-temperature melting capacity and ultimately high-productivity. Recoater 714 may feed new metallic powder from powder container 712 to build area 716, where electron beam 708 may melt the metallic powder for building up of part.

As a reference, examples of differences between EBM and DLM processing are summarized in Table 2, below. While EBM and DLM are discussed herein as examples of 3D printing, the method disclosed herein is not limited to these particular examples, and may be utilized with other 3D printing methods known and not yet known. The outermost layer of coated powder composite 100 may be modified differently to be adapted for each specific 3D printing method.

TABLE 2

Differences between EBM and DLM processing

| Characteristic | Electron Beam Melting | Direct Laser Melting |
| --- | --- | --- |
| Thermal Source | Electron Beam | Laser |
| Atmosphere | Vacuum | Inert Gas |
| Scanning | Deflection Coil | Galvanometers |
| Energy Absorption | Conductivity Limited | Absorptivity Limited |
| Powder Preheating | Uses Electron Beam | Uses Infrared Heaters |
| Scan Speed | Very fast, magnetically driven | Limited by galvanometer inertia |
| Energy Cost | Moderate | High |
| Surface Finish | Moderate to Poor | Excellent |
| Feature Resolution | Moderate | Excellent |
| Materials | Metals | Polymers, metals, ceramics |

The test coupons of step 304 may be 4 to 6" wide coupons suitable for mechanical and other physical testing to determine property data.

Figure 8B:
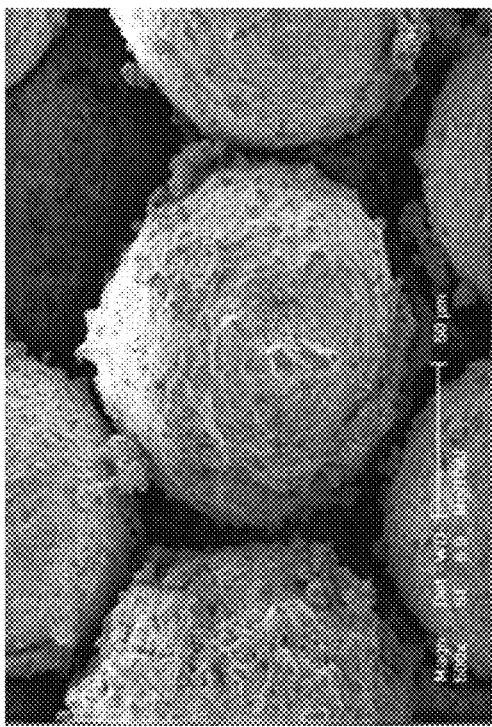
FIGS. 8A-8C are micrographs of different Mg-powder compositions suitable for use in the coated powder composite, products and methods of the present disclosure.
Figure 8A:
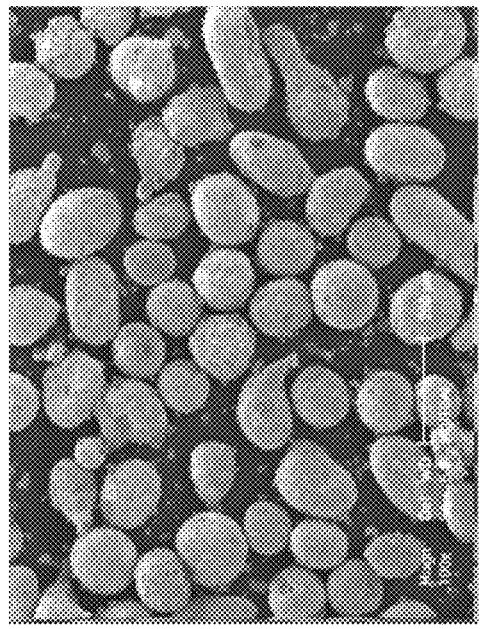
Figure 8C:
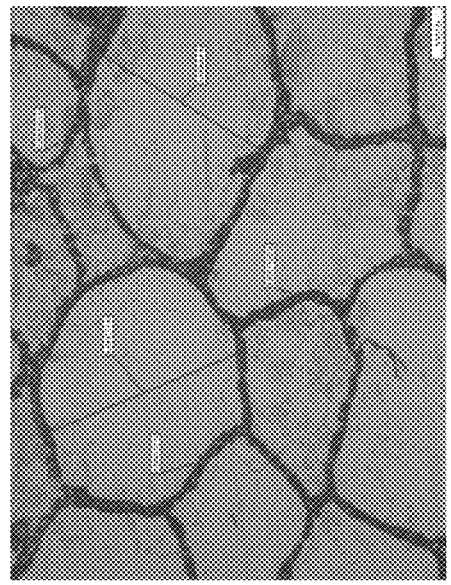

In step 306, powder and parts materials characterization may be performed. Characterization of the powders before and after coating may be performed. Characterization may be performed using: X-ray fluorescence (XRF) of powders and solid parts; cross-sectional thickness analysis; scanning electron microscopy (SEM)/EDAX evaluation of particles and X-sections; and X-ray diffraction (XRD). Examples of SEM characterization is shown in FIGS. 8A-8C. FIG. 8A is an SEM image of a coated Mg powder, FIG. 8B is an SEM image of an Al coated Mg powder, and FIG. 8C is an SEM image of an APS consolidated Mg.

Once an optimum alloy composition is selected, powders may be synthesized and then additively manufactured to form bulk components.

To quantify the effect of the proposed processing techniques, mechanical testing may be performed to quantify the alloy's tensile and compressive properties. As-cast, homogenized, and extruded samples of selected alloy compositions may be machined into requisite shapes following ASTM standards using a mill and lathe, for example. Such samples may then be tested using an Instron 5582 electro-mechanical universal testing machine using laser and clip on extensometers, for example. This testing may be performed in concert with hardness testing, using a Buehler Vickers hardness indenter, for example. Resultant data may include, but is not limited to: modulus, yield strength, tensile strength, strain hardening behavior, and strain rate sensitivity.

Assessments on the degradation characteristics of our selected powder alloys and/or coated powder composites may be conducted through controlled in vitro degradation studies. For example, the release and dissolution of alloy degradation products from the bulk Mg alloys may be assessed over time. Samples of the materials, including polylactic acid (PLLA) controls, may be incubated at 37° C. in simulated body fluid, such as Hank's balance salt solution. The incubation fluid may be changed every 24 hours to mimic the mechanism by which the joint removes foreign entities. As such, SEM, cross-sectional analysis, and surface characterization of powders and consolidated parts may be performed.

In step 308, results may be analyzed. After the completion of microstructural and mechanical property characterizations, a test structure may be designed and fabricated using a powder bed fusion system. After deposition, and any desired follow-on heat treatment, is completed, the part may be inspected for the presence of defects, such as internal porosity. A dimensional inspection may also be performed to characterize the ability of the process to produce part features and to maintain required dimensional tolerances.

Product Made from the Composite and Method of Making the Same

Certain embodiments relate to products made from any of the embodiments of powder coated composite 100 disclosed herein. In some embodiments, the product may be a biodegradable implant. For example, the biodegradable implant may be adapted to provide structural support, and to be reabsorbed into the body after completion of the healing process. Biodegradable implants may prevent the need for a second surgery for implant retrieval. In certain embodiments, the implants disclosed herein are both biocompatible and bioabsorbable.

Figure 9:
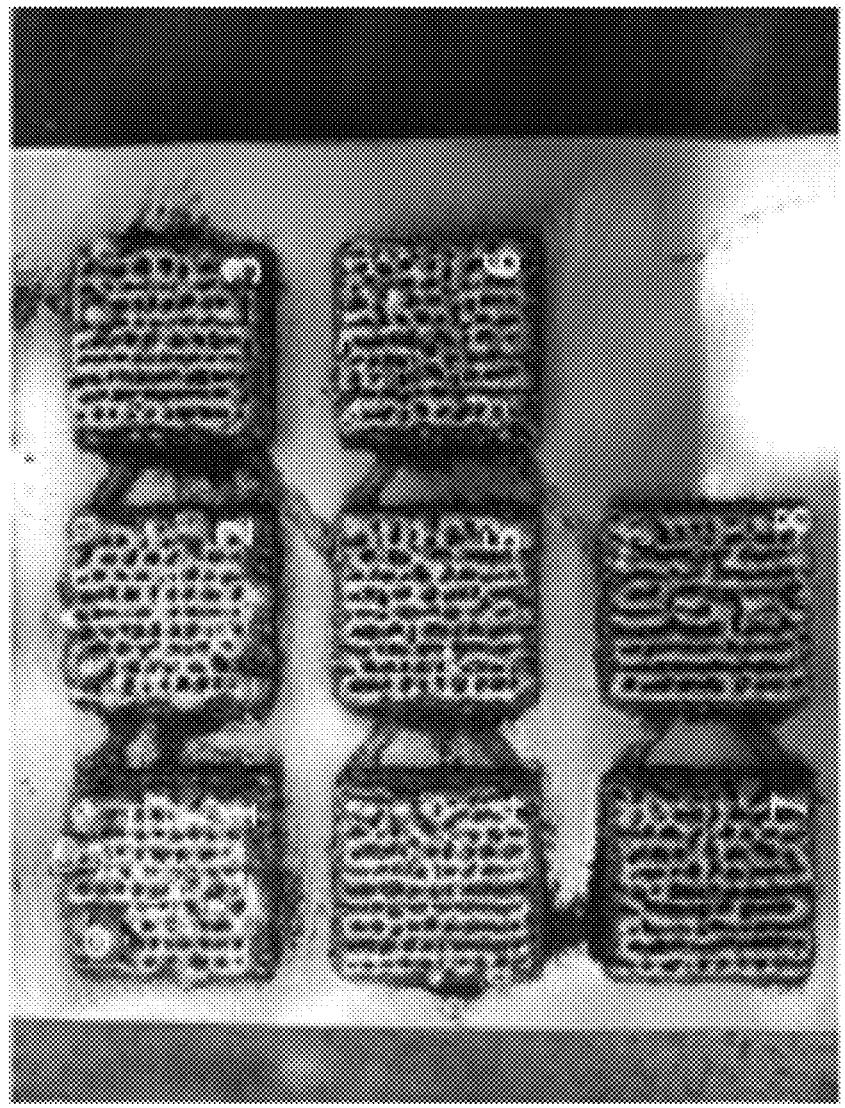
FIG. 9 is an image of an example of a product or sample of a product made in accordance with the present disclosure.

In some embodiments, the products disclosed herein are structural components, such as dental implants, pins, plugs, limb replacements, limb joinings, acetabular (hip) cups, orthopedic screws and fixation plates for knees, shoulder trauma implants, fingers and toes implants, scaffolding for spinal fusion, scaffolding for hip and femur trauma, craniomaxillofacial implants, stents, or other orthopedic implant products. In some embodiments, the product is a net shaped structure and/or a porous structure that enable for bone growth. Such porous products may increase bone attachment and replacement (surface area). For example, the implant may be a trabecular structure, which is a fine, lattice shaped structure that allows living bone to fuse to the implant, such as via osseo-integration. FIG. 9 depicts an example of a sample product formed of a coated powder composite in accordance with certain embodiments of the present disclosure having a magnesium core particle, a layer of Fe, and an outermost layer of Ca.

Figure 10:
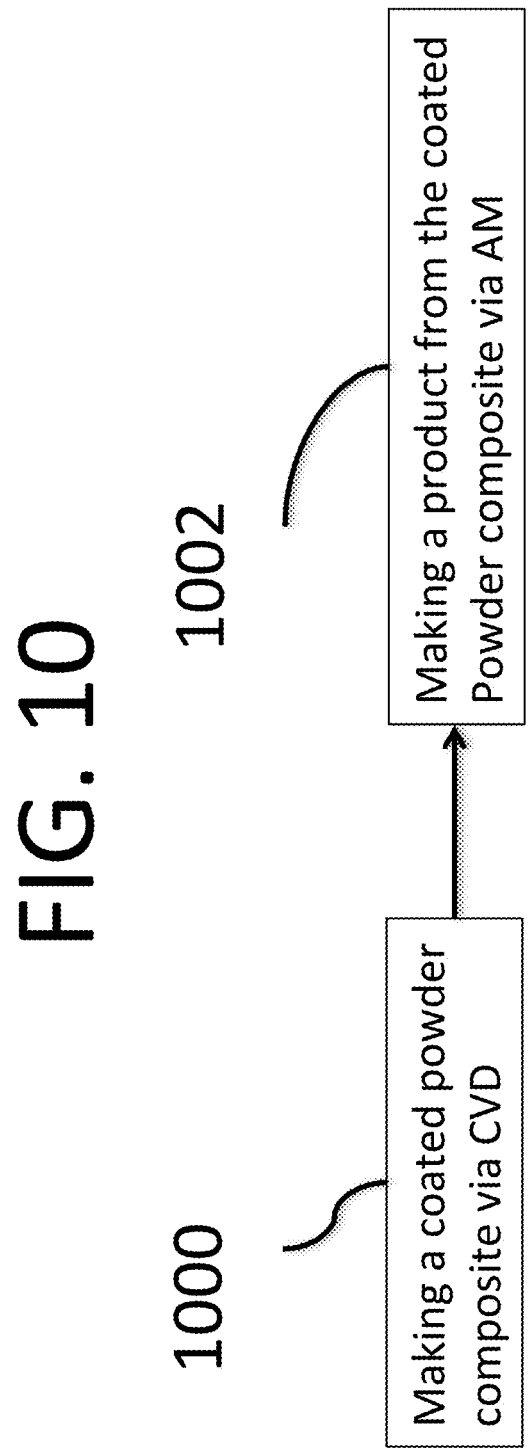
FIG. 10 is a flow chart of a method of making a product in accordance with the present disclosure.

In some embodiments, the product is formed via a one step process of additive manufacturing, as described herein. For example, with reference to FIG. 10, a method may include making a coated powder composite via chemical vapor deposition, 1000. Use of a CVD fluid bed reactor may allow for control of the surface reactions and material distribution on coated powder composite 100 and products made therefrom. The method may include making a product from the coated powder composite via additive manufacturing, 1002. In AM, the product may be made into a desired shape directly from a shape defined by a CAD program, for example. As such, individually customize internal bone components may be formed.

Medical implants made in accordance with the present disclosure may exhibit controlled degradation, such that the medical implants remain in the body only as long as needed; thereby minimizing allergy and sensitization issues. Medical implants made in accordance with the present disclosure may not require removal by surgery; thereby enhancing patient comfort and lowering costs.

In some embodiments, when combined with materials such as calcium and strontium, the implant composition may promote bone formation and compatibility; thereby speeding patient recovery. The material compositions of the medial implants may mimic natural bone; thereby resulting in greater implant stability and decreased risk to healthy bone tissue from stress shielding. Additionally, the medical implants disclosed may decrease reduction in bone density (osteopenia) as a result of removal of normal stress from the bone by an implant. Such advantages, coupled with the benefits of Mg encapsulated powders discussed herein, may provide an advantageous, engineered, bio-compatible and controlled dissolving Mg medical implants.

In some embodiments, products made in accordance with the present disclosure have a high strength/weight ratio. In some embodiments, non-implant applications and or products may be formed from coated powder composite 100 disclosed herein via AM processing. In some such embodiments, the product is a non-dissolving product. Such embodiments include, but are not limited to, external devices such as knee braces, foot braces, elbow braces, surgical tools (optionally with integrated cooling channels), and artificial limbs. Non-medical products that may be produced include products for use in the oil and gas industry, aerospace industry, high performance auto industry, and high performance sport industry, such as tennis rackets, golf clubs, fishing reels, archery equipment, and the like.

In certain embodiments, products made in accordance with the present disclosure are biocompatible, biodegradable, lightweight, have higher strength-to-weight ratios, low cost, have tailorable properties, have controllable dissolution/absorption rates for human use, or combinations thereof. In some embodiments, the rate of dissolution of the product within the human body may be constant or substantially constant.

In some embodiments, AM printed products formed in accordance with the present disclosure are dental implants. 3D printing implemented in the manufacturing dental implants may be used to form porous structures that enable bone growth.

Coated powder composite 100 (e.g., Al/Mg powders) may be sintered utilizing a 3D printing technique. As previously described, products may be formed using AM techniques and systems, Concept Laser, and a Robotic Laser Deposition systems. In some embodiments, surface modifications of powders may result in 35-45% increase in strength performance, providing coated powder composite 100 with an at least 50 ksi tensile strength prior to heat treatment, for example.

An example of a coated powder composite 100 for use in bio-compatibility applications is one having an Mg core particle with an intermediate layer of coating of Sr, and an outermost layer of coating of Ca. In some embodiments, the dissolve/degradation rate of coated powder composite 100 may be modified by additions of 0.1-0.8 wt % of dissolution activator.

The methods disclosed herein provide techniques for AM consolidation of the core particle (e.g., Mg) and controlling the degradation rate for the particular application. One challenge for AM processing of lightweight reactive materials, such as Mg and Al, is controlling the surface and environment of the process. The reflective nature, low density and high thermal diffusivity of such powders, combined with the controlled inert environment required, makes consolidation and control difficult in many systems using Al and Mg based materials. In addressing this challenge, different coatings on the core particle 110, such as Si, Zn and others, are provided that enable for the controlled consolidation of the coated powder composite 100 in an inert environment such as EOS, DMLS, and ARCAM's Ion Beam systems. Historically, the lack of control over the Al or Mg powder surface has created porous, low strength (tensile strength of 25-30 ksi) materials. However, AM materials formed in accordance with the present disclosure have demonstrated tensile strengths of Al ranging from 53-55 ksi and of Mg of from 40-47 ksi. Also, ductility achieved in tensile testing for both Al and Mg was demonstrated at from 10-12%.

Successful control of degradation and dissolution of Mg may be projected from controlled dissolution rates designed and achieved of degradable hydraulic fracturing balls of similar compositions in the range of 1-3600 mg/cm2/hr in various fluids (e.g., water, KCl, HCl) at room temp to 200° F. The control of the Mg chemistry and layers of dissimilar materials controls the electrolytic dissolution of these materials. For Mg-based medical implants, the coated powder composite 100 may be tailored, by way of coating systems or layer design (coatings 120), to the human body solutions encountered.

The control of the nano-layers and the resultant composition of coated powder composite 100 allow for the engineered composites to achieve desired material performance, such as improved AM processing, strength, degradation-dissolve rate, density, and other properties. The evenly distributed metal-coated particles of coated powder composite 100 enable greater uniformity, control of surface reactions (capor pressures, oxide formation), and control of reactions/eutectic formation for compositions with the encapsulated powders. The interface layer of coated powder composite 100 may enhance the processing thereof and final performance properties of coated powder composite 100. The control of the layers of coated powder composite 100 allows for production of different dissolvable or degradable Mg materials and provides energy absorption at the powder surface to control rapid eutectic formation to make high strength composites. Further, the addition of metal additives in amounts ranging from 0.10%-0.5%, for example, may have an impact in the degradation rate of the Mg. As such, control of the degradation rate within +/−0.05% may be achieved.

Additive Manufacturing (AM)

AM has several advantages over traditional manufacturing, including almost zero waste, zero emissions, and use of much less energy and limited resources to produce parts. AM does not directly use of toxic chemicals, such as lubricants or coolants. AM directly converts 3D models into a finished part. AM is an approach for making high strength, complex shaped metal parts for many applications and provides a platform for fabricating net shape and near net-shape metal components directly from a powder or wire feed stock.

With reference to FIG. 6 and the AM process illustrated therein, a component is built up layer-by-layer by fusing each layer to the previous one through the interaction between the feed stock material and a high energy density heat source, such as a laser or electron beam. The deposited material undergoes a series of non-uniform thermal cycles during processing, resulting in anisotropic and location-dependent material properties. For AM components to be used in structural applications, it is desirable to be able to reliably predict the mechanical properties thereof, such as the large deformation plastic behavior and fracture properties, of the part developed for different material systems. Parts may be designed in view of the connection between the thermal history, material microstructure, and final mechanical properties. Applications for AM technologies range from the production of critical aerospace components to personalized medical implants or devices.

Ti and Ni alloys have mechanical properties primarily controlled by a diffusion driven allotropic phase transformation that occurs during forming or deposition. The ability of these materials to absorb the energy used to melt and sinter the powders has made these more attractive to manufacture than lighter Al or Mg or Ca materials. However, through control of the surface of coated powder composite 100, high strength Mg, Ca, and Al products may be made using AM techniques.

In some embodiments, coated powder composite 100 is processed with AM to fabricate orthopedic implants (or test coupons thereof). The coated powder composite 100 may be characterized by the biocompatible, degradable, and bioabsorbable properties thereof, but also may be optimized to have desirable mechanical and other properties achieved and available through utilizing Mg-based powders and AM techniques.

In some embodiments, initial deposition conditions (CVD) avoid partial or excessive melting and ensure proper melting conditions of engineered powders experimentally by varying powders and scan speeds and optimizing process parameters for AM techniques In some embodiments, the method of making products may include hot isotactic pressing (HIP) after AM to close porosities in the product. In some embodiments, no HIP is used to form porous products.

In some embodiments, the products formed herein may be subjected to heat treatment, which may include solution annealing, cooling, and ageing.

The microstructure of the products disclosed herein may be characterized by Optical/SEM. Certain properties of the products disclosed herein that may be characterized include the phases present in by XRD, various mechanical properties, hardness, and Charpy Impact. Degradation measurements of the products may be performed in Hank's solution (a composition close to simulated body fluid) at 37° C. Other properties of the products disclosed herein that may be characterized include stress-corrosion cracking, corrosion fatigue and cytotoxicity.

Embodiments of the methods disclosed herein allow for fabrication of net-shape engineered high-strength, high-toughness, small-scale, degradable magnesium orthopedic implant components using engineered powder and optimized power/scan speed parameters developed for different AM processes.

The method may be used to form engineered nano-layered metals (e.g., Ca/Sr/Si/Zn coated Mg alloy powders) with low ppm oxygen, such as below 800 ppm, below 600 ppm, or below 400 ppm oxygen; low cost; high strength; and controlled dissolution using rapid fabrication by AM. In some embodiments, the coated powder composite 100 or product made therefrom is subjected to a Hydrogen cleaning step to reduce any oxides.

Certain embodiments relate to a method that includes providing a core particle, encapsulating the core particle with one or more layers of metals (pure or alloy) and/or metal oxides, forming a coated powder composite, and using additive manufacturing to build a medical implant product from the coated powder composite. The core particle and layers of coating may be selectively tailored to provide the coated powder composite and/or product made therefrom with certain properties, such as strength and degradation properties, as detailed herein.

Medical Implant Design Goals

Figure 11:
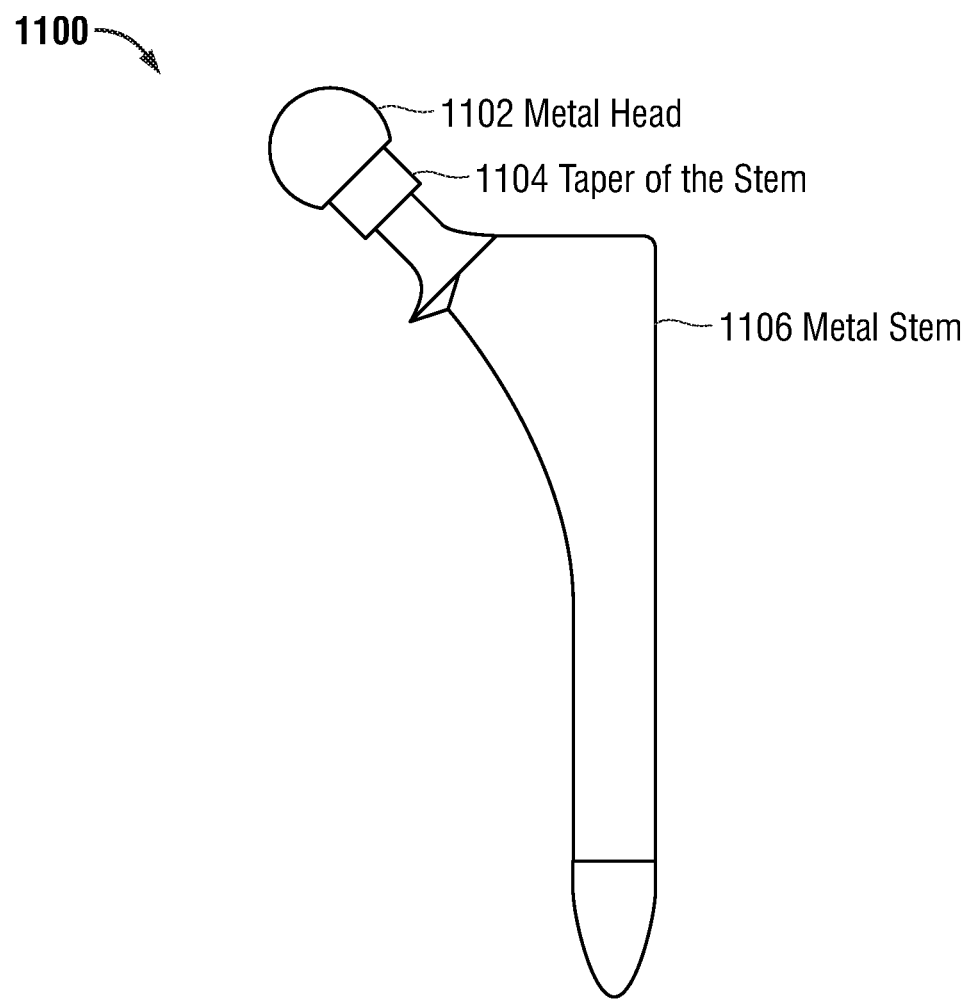
FIG. 11 is an image of an example of a product made in accordance with the present disclosure.
Figure 12:
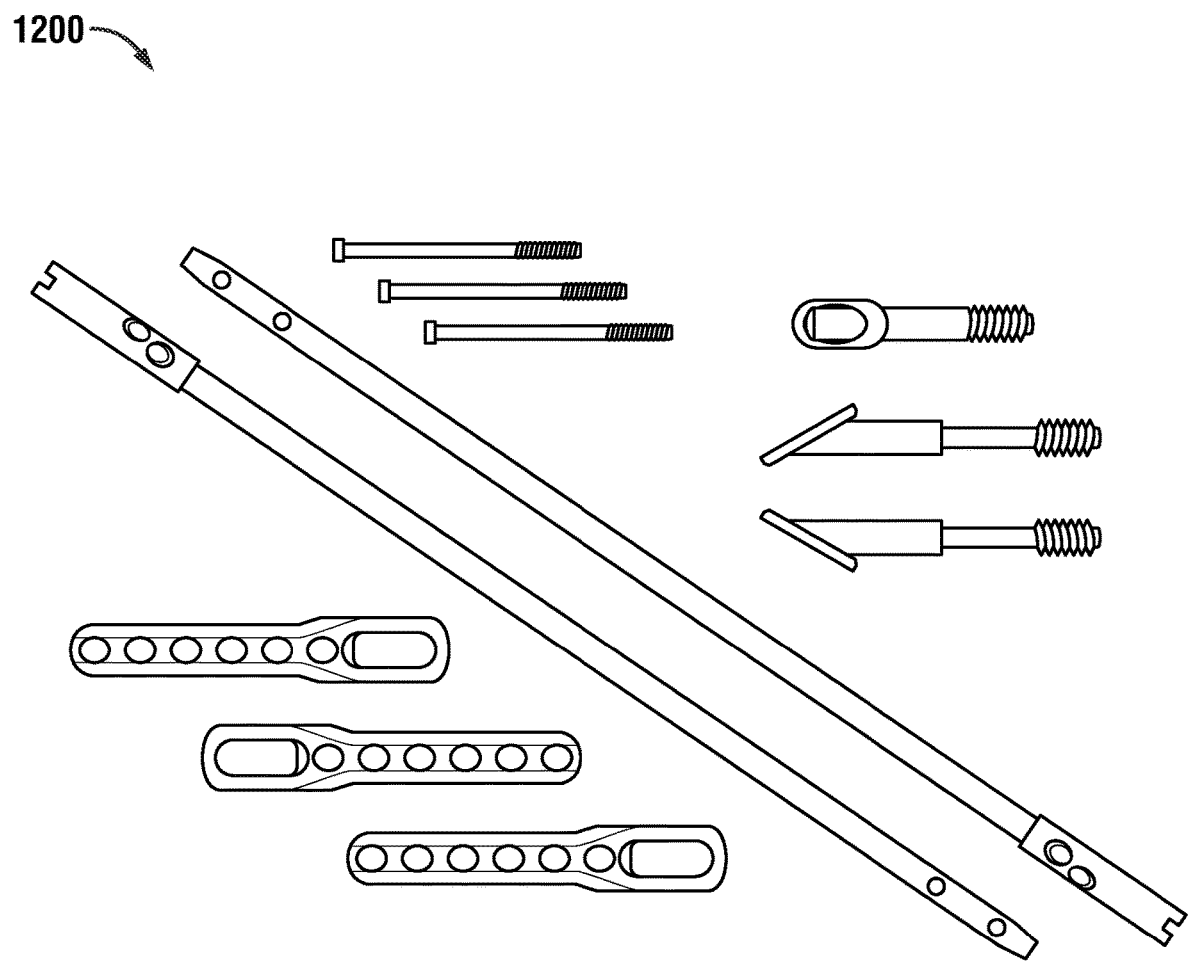
FIG. 12 is an image showing multiple examples of products made in accordance with the present disclosure.

In certain embodiments, the products formed herein are magnesium-based due to displacement of the Mg by Ca and absorption of the Mg into the body. Some examples of products include screws and pins (e.g., for use with bones), dental layers, and bones. Examples of products are shown in FIGS. 11 and 12. FIG. 11 shows product 1100 with metal head 1102, taper of stem 1104, and metal stem 1106. FIG. 12 shows various exemplary products 1200.

Products disclosed herein may be adapted maintain structural integrity during manufacture processes (e.g., AM), cleaning processes (e.g., sonic cleaner), sterilization (e.g., heat-autoclave), packaging (e.g., vacuum packaging), overcoating (e.g., hydroxyapatite), temperatures of 37 degrees Celsius, a pH of 7.4, and contact with human tissue. Products disclosed herein may be designed to not exhibit cytotoxicity. FIG. 11 is sourced from: http://www.bing.com/images/search?view=detailV2&ccid=2iVP4DBg&id=EE02837F3C9B5946875C5FD31F712A10D4F13C0B&q=implant+pictures+femur&simid=608031026775590982&selectedIndex=55. FIG. 12 is sourced from: http://www.bing.com/images/search?view=detailV2&ccid=cB4O46w9&id=378F00EC57AA170F4AE6330C5CD1A5C2F7B2-F00C&q=Ortho+Implants&simid=607995112265420584&selectedIndex=11.

In some embodiments, the products disclosed herein may have a tensile strength of from 10-11 ksi, a tension modulus of from 5-6 MSI, exhibit a compression 12-30 ksi, a compression modulus of 11 MSI, and a ductility up to 3%; thereby approximating properties of human bone.

Table 3 lists results for certain properties for different embodiments of medical implants coupons. The coated powder composite used in the samples in Table 3 had a core particle of Mg, a middle layer of Fe, and an outermost layer of Ca. In the embodiments in Table 3, the weight percent of Fe, the dissolution activator, increase from the composition in the uppermost row to the composition in the lowermost row.

TABLE 3

Magnesium Medical Implant Results
Mag/Fe/Ca

| Mag/Fe/Ca | Tensile | | Compression | |
|---|---|---|---|---|
| Porosity | UTS (ksi) | Ductility % | UTS (ksi) | Ductility % |
| 7 | 31-32 | 11-12 | 38-40 | 9-11 |
| 15 | 25-28 | 9-10 | 30-35 | 6-8 |
| 25 | 16-18 | 5-6 | 20-22 | 4-5 |

Table 4 lists dissolution rates for different embodiments of medical implant coupons. The coated powder composite used in the samples in Table 4 had a core particle of Mg, a middle layer of Fe, and an outermost layer of Ca.

TABLE 4

Dissolution Rates

| Composition | Dissolution Rate |
|---|---|
| Mg/Fe/Ca (Comp 1) | 0.003 mg/cm$^2$/hr |
| Mg/Fe/Ca (Comp 2) | 1.3 mg/cm$^2$/hr |
| Mg/Fe/Ca (Comp 3) | 3.9 mg/cm$^2$/hr |

The coated powder composite used in the samples in Table 4 had a core particle of Mg, a middle layer of Fe, and an outermost layer of Ca. In the embodiments in Table 4, the weight percent of Fe, the dissolution activator, increase from the composition in the uppermost row to the composition in the lowermost row. The dissolution test was performed at 37 degrees Celsius, a pH of 7.4, for 24 hours.

Galvanic Cells

Figure 14:
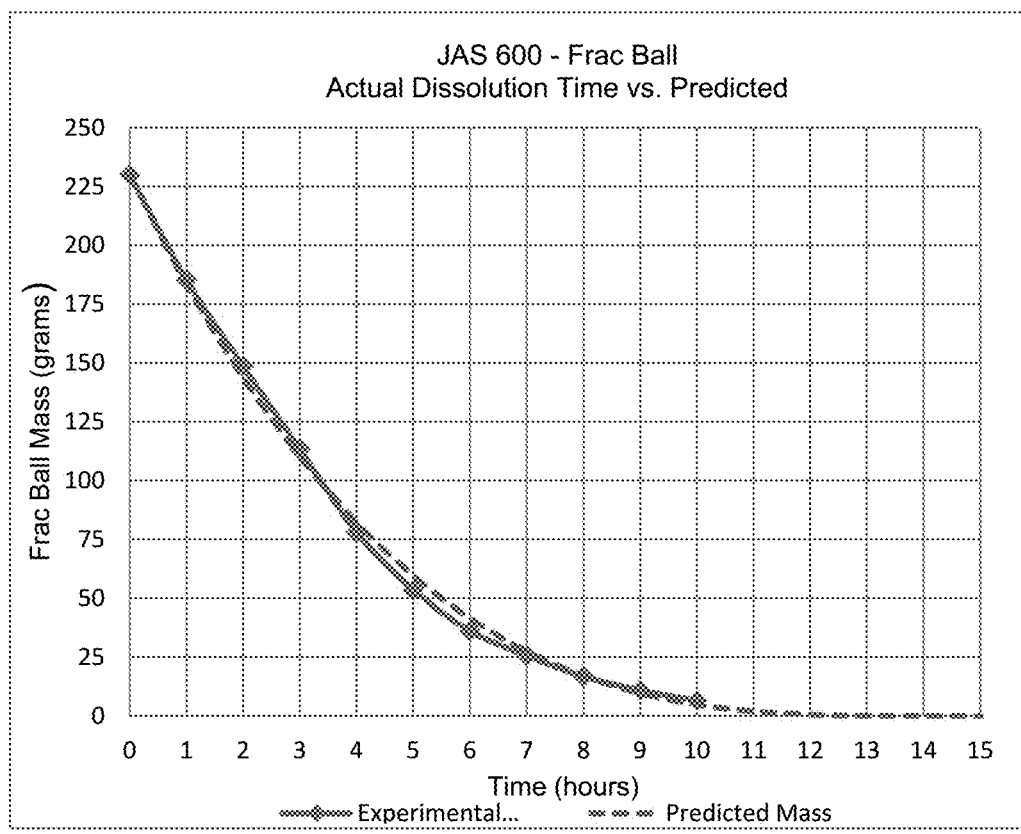
FIG. 14 is a graph of a typical dissolution rate.

In some embodiments, the layers of coating 120 of coated powder composite 100 is designed and/or arranged adjacent layers exhibit an electrical potential, initiating galvanic corrosion of the layers of coatings 120. By selectively controlling the constituents of each layer, the arrangement of the layers, and the thickness of each layer of coating 120, the galvanic corrosion of the particles of the coated powder composite 100 and the products made therefrom may be tailored. Control of the degradation rate may allow for products to be implanted into the human body without releasing metals, such as Mg, at too high of a rate into the human body. For example, release of Mg at too high of a rate into the human body may result in illness or death. In some embodiments, the layers of coating (composition, thickness, arrangement) may be controlled to provide a target dissolution rate of the product within the human body. The rate at which Mg is released by coated powder composite may be adapted to be less than or equal to the maximum rate that the human body can process Mg. FIG. 14 is a graph of a typical dissolution rate for a frac ball over time (both actual and predicted) in grams per hours. The dissolution rate of products disclosed herein within the human body may be substantially constant.

Products made from coated powder composite 100 may be a substantially, compositionally uniform throughout on a macroscopic level, while each coated powder composite 100 that forms the product varies in material composition from layer to layer at the micron and/or nanometer level. In some embodiments, some or each layer of coating 120 is substantially, compositionally uniform throughout.

Figure 13:
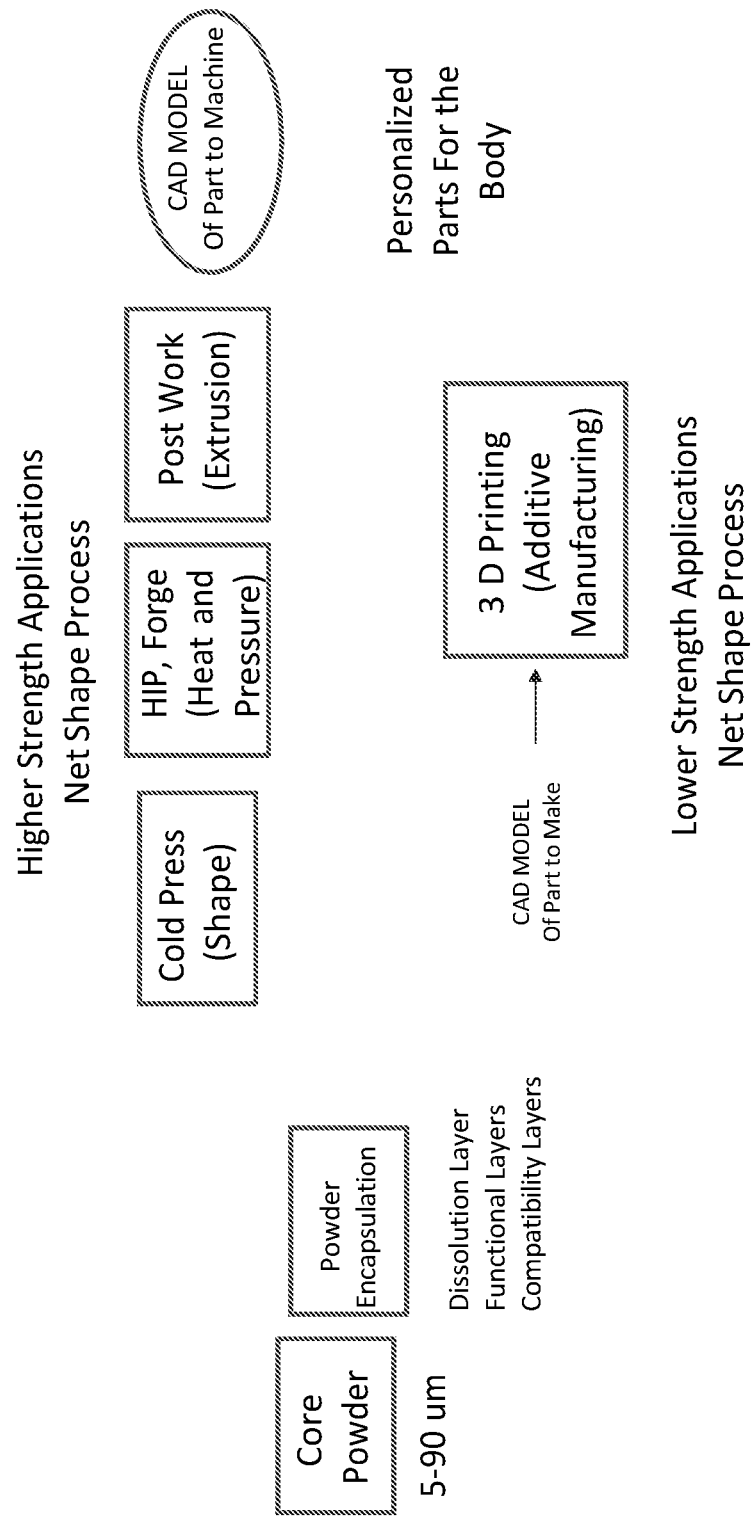
FIG. 13 is a flow chart of a method of making a product in accordance with the present disclosure.

FIG. 13 depicts a flow chart showing a method of forming products in accordance with certain embodiments. The method may include providing a core powder for the core particle; and encapsulating the core powder with one or more dissolution layers, functional layers, and/or biocompatibility and AM-compatibility layers, forming a coated powder composite.

For higher strength applications, the method may include cold pressing the coated powered composite to a desired shape, HIP processing and forging using heat and pressure, and post work extrusion processing as needed, followed by CAD aided machining of the part for a custom/personalized product for the patient.

For lower strength applications, the method may include CAD modeling the part to be made, and 3-D printing (AM) the part based on the CAD model.

In some embodiments a scan (such as an X-ray) of the relative portion of a patient (such as a broken bone) may be taken to form a CAD file or the like, from which the product made herein may be 3D printed.

Unless otherwise indicated, all testing methods and associated properties discussed and disclosed herein are performed or determined in accordance with ASTM International.

Although the presently disclosed product, system and\or process and their advantages have been described in detail, it should be understood that various changes, substitutions and alterations can be made herein without departing from the spirit and scope of the disclosure and as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical implant comprising:
a material composition, the material composition comprising a matrix of coated core particles, wherein each coated core particle comprises a core particle and multiple coating layers disposed about said core particle;
wherein the core particles comprise Mg or an alloy or oxide thereof, or Ca or an alloy or oxide thereof, or Al or an alloy or oxide thereof; and
wherein the multiple coating layers comprise an innermost coating layer comprising a dissolution activator comprising Fe, Mg, C, Cu, or alloys thereof; an outermost coating layer comprising Ti, C, or alloys thereof; and at least one intermediate coating layer positioned between the innermost coating layer and the outermost coating layer, the at least one intermediate coating layer comprising Al, Zn, Al$_2$O$_3$, Ca, Ti, C, Sr, or combinations thereof;
wherein each coating layer exhibits electrical potential relative to an adjacent coating layer of the multiple coating layers; and
wherein the outermost coating layer is biodegradable in a human body at a first dissolution rate, wherein the innermost coating layer is biodegradable in the human body at a second dissolution rate, wherein the at least one intermediate coating layer is biodegradable in the human body at a dissolution third rate, and wherein the first, second and third dissolution rates are different, and wherein the material composition is biodegradable in the human body at a constant or substantially constant dissolution rate.

2. The medical implant of claim 1, wherein the at least one intermediate coating layer provides mechanical strength to the coated core particle, wherein the dissolution activator comprises a compound or element capable of activating dissolution of the material composition within a human body, and wherein the outermost layer comprises a composition that is suitable for use in additive manufacturing and is biocompatible within the human body.

3. A medical implant comprising:
a material composition, the material composition comprising a matrix of coated core particles, wherein each coated core particle comprises a core particle and multiple coating layers disposed about said core particle;
wherein the multiple coating layers comprise an innermost coating layer comprising a dissolution activator comprising Fe, Mg, C, Cu, or alloys thereof; an outermost coating layer comprising Ni, Fe, Ti, Cu, Si, Al, Co, C, Ca, Zn, or alloys thereof; and at least one intermediate coating layer positioned between the innermost coating layer and the outermost coating layer, the at least one intermediate coating layer comprising Al, Zn, Al$_2$O$_3$, Ca, Ti, C, Sr, or combinations thereof; and
wherein said core particles comprise bone or a material derived from bone.

4. The medical implant of claim 1, wherein said core particles comprise Mg or an alloy or oxide thereof, or Ca or an alloy or oxide thereof.

5. The medical implant of claim 1, wherein the multiple coating layers comprise a coating layer of Sr or an alloy or oxide thereof, a coating layer of Ca or an alloy or oxide thereof, a coating layer of Si or an alloy or oxide thereof, a coating layer of Zn or an alloy or oxide thereof, a coating layer of Mg or an alloy or oxide thereof, a coating layer of Al or an alloy or oxide thereof, a coating layer of Fe or an alloy or oxide thereof, a coating layer of Ni or an alloy or oxide thereof, a coating layer of Ti or an alloy or oxide thereof, a coating layer of Cu or an alloy or oxide thereof, or a coating layer of C.

6. The medical implant of claim 1, wherein the core particles comprise Mg or an alloy or oxide thereof.

7. The medical implant of claim 6, wherein the at least one intermediate coating layer comprises Sr or an alloy or oxide thereof, or further comprises Fe or an alloy or oxide thereof.

8. The medical implant of claim 1, wherein the thickness of all coating layers combined ranges from 5 nanometers to 1.5 microns, and wherein each core particle has a particle size ranging from 5 microns to 200 microns.

9. The medical implant of claim 1, wherein the outermost coating layer constitutes from 0.5 to 10 weight percent of each coated core particle, wherein the at least one intermediate coating layer constitutes from 0.1 to 10 weight percent of each coated core particle, wherein the innermost coating layer constitutes from 0.001 to 8 weight percent of each coated core particle, and wherein the core particle constitutes from 80 to 99 weight percent of each coated core particle.

10. The medical implant of claim 1, wherein said material composition is characterized by a substantially uniform dissolution rate.

11. The medical implant of claim 1, wherein the medical implant exhibits a residence time within a human body that ranges from 1 day to 1 year.

12. The medical implant of claim 1, wherein the material composition is porous.

13. The medical implant of claim 1, wherein the material composition is non-porous.

14. The medical implant of claim 1, wherein the medical implant comprises a dental implant, pin, plug, limb replacement, limb joining, acetabular cup, orthopedic screw and fixation plate for knees, shoulder trauma implant, finger or toe implant, scaffolding for spinal fusion, scaffolding for hip and femur trauma, cranio-maxillofacial implant, stent, or trabecular structure.

15. The medical implant of claim 1, wherein the material composition of the medical implant exhibits a tensile strength of from 10 to 11 ksi, a tension modulus of from 5 to 6 MSI, a compression of from 12 to 30 ksi, compression modulus of about 11 msi, and a ductility of up to 3 %.

16. The medial implant of claim 1, wherein the medical implant is an additively manufactured medical implant for implantation into a human body,
wherein the innermost coating layer is disposed about an outside surface of said core particle;
wherein the core particles comprise Mg or an alloy or oxide thereof or Ca or an alloy or oxide thereof;
wherein the medical implant includes a plurality of fused layers of the material composition, and wherein the medical implant is biocompatible within a human body.

17. The medical implant of claim 1, wherein the medical implant comprises a plurality of fused layers of the material composition.

18. The medical implant of claim 17, wherein the medical implant is formed by subjecting the coated core particles to additive manufacturing, including melting the coated core particles, to fuse the layers of the material composition in a shape of the medical implant.

19. The medical implant of claim 1, wherein the innermost coating layer comprises a dissolution activator comprising Fe, C, or alloys thereof.

20. A medical implant for implantation into a human body comprising:
- a material composition, the material composition comprising a matrix of coated core particles, wherein each coated core particle comprises a core particle and multiple coating layers disposed about said core particle;
- wherein the core particles comprise Mg or an alloy or oxide thereof, or Ca or an alloy or oxide thereof, or Al or an alloy or oxide thereof; and
- wherein the multiple coating layers comprise an innermost coating layer comprising a dissolution activator; an outermost coating layer; and at least one intermediate coating layer positioned between the innermost coating layer and the outermost coating layer; and
- wherein the outermost coating layer comprises Ti, C, or alloys thereof.

21. The medical implant of claim 1, wherein the at least one intermediate coating layer comprises $Al_2O_3$, Ti, C, Sr, or combinations thereof.

22. The medical implant of claim 17, wherein the innermost coating layer comprising a dissolution activator comprising Fe, Mg, C, Cu, or alloys thereof and the at least one intermediate coating layer comprises Al, Zn, $Al_2O_3$, Ca, Ti, C, Sr, or combinations thereof.

* * * * *

UNITED STATES PATENT AND TRADEMARK OFFICE
CERTIFICATE OF CORRECTION

PATENT NO. : 11,109,976 B2
APPLICATION NO. : 15/464226
DATED : September 7, 2021
INVENTOR(S) : Dean M. Baker Page 1 of 1

It is certified that error appears in the above-identified patent and that said Letters Patent is hereby corrected as shown below:

In the Specification

Column 1, Line 19, delete "compositions" and insert --composition--.
Column 4, Line 38, delete "be".
Column 6, Line 17, delete "a".
Column 15, Line 15, delete "capor" and insert --vapor--.
Column 16, Line 18, delete "ageing" and insert --aging--.
Column 16, Line 22, delete "by".
Column 16, Line 62, insert --to-- after the word "adapted".
Column 17, Line 60, delete "is" and insert --are--.
Column 17, Line 61, insert --to-- after the word "layers".

In the Claims

Column 19, Line 28, delete "dissolution third rate," and insert --third dissolution rate--.
Column 19, Line 38, insert --coating-- between "outermost" and "layer".
Column 21, Line 22, delete "comprising" and insert --comprises--.

Signed and Sealed this
Twentieth Day of June, 2023

Katherine Kelly Vidal
*Director of the United States Patent and Trademark Office*